(12) United States Patent
Bruce et al.

(10) Patent No.: US 7,277,569 B2
(45) Date of Patent: *Oct. 2, 2007

(54) APPARATUS AND METHOD FOR DETECTING AND LOCATING RARE CELLS

(75) Inventors: Richard H. Bruce, Los Altos, CA (US); Douglas N. Curry, Menlo Park, CA (US); Robert T. Krivacic, San Jose, CA (US); Huangpin B. Hsieh, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1042 days.

This patent is subject to a terminal disclaimer.

(21) Appl. No.: 10/616,366

(22) Filed: Jul. 9, 2003

(65) Prior Publication Data

US 2004/0071332 A1    Apr. 15, 2004

Related U.S. Application Data

(63) Continuation-in-part of application No. 10/271,347, filed on Oct. 15, 2002, now Pat. No. 7,113,624.

(51) Int. Cl.
*G06K 9/00* (2006.01)
(52) U.S. Cl. .................... 382/133; 382/128; 382/132
(58) Field of Classification Search ............... 382/128, 382/129, 130, 131, 132, 133, 134; 356/3.02, 356/3.04, 3.06, 73, 73.1, 139.1, 139.03; 378/98.8, 378/98.3, 98.4, 98.6, 98.9; 600/160, 178, 600/181, 182, 476, 478
See application file for complete search history.

(56) References Cited

U.S. PATENT DOCUMENTS 4,002,829 A    1/1977    Hutchison (Continued)

FOREIGN PATENT DOCUMENTS

| GB | 1 579 188 | 11/1980 |
|----|-----------|---------|
| JP | 4296642   | 10/1992 |
| JP | 6148085   | 5/1994  |
| JP | H9-145631 | 6/1997  |

OTHER PUBLICATIONS

European Search Report, dated Apr. 5, 2006; EPC Application No. 05112479.0-2204, Berlin.

(Continued)

*Primary Examiner*—Samir Ahmed
*Assistant Examiner*—Abolfazl Tabatabai
(74) *Attorney, Agent, or Firm*—Fay Sharpe LLP

(57) ABSTRACT

In accordance with one aspect of the present application, an imager and method for detecting and locating rare cells in a sample is disclosed. An imager stage supports the sample. A fiber optic bundle has a proximate bundle end of first fiber ends arranged to define an input aperture viewing the sample on the translation stage. The fiber optic bundle further has a distal bundle end of second fiber ends arranged to define an output aperture shaped differently from the input aperture and disposed away from the imager stage. A scanning radiation source is arranged in fixed relative position to the input aperture. The scanning radiation source scans a radiation beam on the sample within a viewing area of the input aperture. The radiation beam interacts with the sample to produce a light signal that is reflected, scattered, transmitted, re-emitted, or otherwise collected and received by the input aperture and transmitted via the fiber optic bundle to the output aperture. The scanning radiation source rasters the radiation beam over a selected area of the sample. A photodetector is arranged to detect the light signal at the distal bundle end, and a processor processes the detected light signals.

33 Claims, 12 Drawing Sheets

U.S. PATENT DOCUMENTS

| | | | |
|---|---|---|---|
| 4,010,364 | A | 3/1977 | Fuwa |
| 4,556,903 | A | 12/1985 | Blitchington et al. |
| 4,600,951 | A | 7/1986 | Blitchington |
| 4,721,851 | A | 1/1988 | Kogure |
| 4,849,645 | A | 7/1989 | Mendenko et al. |
| 4,875,780 | A | 10/1989 | Moran et al. |
| 4,941,309 | A | 7/1990 | Fluent et al. |
| 5,017,798 | A | 5/1991 | Murakami et al. |
| 5,216,485 | A | 6/1993 | Bird et al. |
| 5,220,617 | A | 6/1993 | Bird et al. |
| 5,315,993 | A | 5/1994 | Alcala |
| 5,471,066 | A | 11/1995 | Hagiwara |
| 5,627,365 | A | 5/1997 | Chiba et al. |
| 5,640,246 | A | 6/1997 | Castonguay |
| 5,651,047 | A * | 7/1997 | Moorman et al. ......... 378/98.8 |
| 5,732,162 | A | 3/1998 | Curry |
| 5,798,831 | A | 8/1998 | Hagiwara |
| 5,892,577 | A | 4/1999 | Gordon |
| 6,445,451 | B1 | 9/2002 | Douglas-Hamilton et al. |
| 6,545,334 | B2 | 4/2003 | Verhaegen |
| 6,582,363 | B2 * | 6/2003 | Adachi et al. .............. 600/178 |
| 6,636,623 | B2 * | 10/2003 | Nelson et al. .............. 382/133 |
| 2001/0046712 | A1 | 11/2001 | Hang et al. |
| 2002/0177885 | A1 | 11/2002 | Eisfeld et al. |
| 2002/0186368 | A1 | 12/2002 | Rosengaus et al. |
| 2004/0071330 | A1 | 4/2004 | Curry |
| 2004/0131241 | A1 | 7/2004 | Curry et al. |

OTHER PUBLICATIONS

European Search Report, dated Jun. 2, 2006; EPC Application No. 05112370.1-2204.

EP 03 25 6441, European Search Report, Jan. 20, 2004, Berlin.

Bianchi, Diana W., et al., Fetomaternal Cellular and Plasma DNA Trafficking, The Yin and the Yang, *Annals New York Academy of Sciences*, pp. 119-131.

WOLFE, Josh, A Thousand Dots of Light, *Forbes/Wolfe Nanotech Report*, May 29, 2002, www.Forbes.com.

PERTL, Barbara, MD, et al., Fetal DNA in Maternal Plasma: Emerging Clinical Applications, *The American College of Obstetricians and Gynecologists*, Published by Elsevier Science Inc., vol. 98, No. 3, Sep. 2001, pp. 483-490.

Bauer, Kenneth D., et al., Reliable and Sensitive Analysis of Occult Bone Marrow Metastases Using Automated Cellular Imaging, *Clinical Cancer Research*, vol. 6, pp. 3552-3559, Sep. 2000.

Witzig, Thomas E., et al., Detection of Circulating Cytokeratin-positive Cells in the Blood of Breast Cancer Patients Using Immunomagnetic Enrichment and Digital Microscopy, *Clinical Cancer Research*, vol. 8, 1085-1091, May 2002.

Ghossein, R.A., et al., Molecular Detection and Characterisation of Circulating Tumour Cells and Micrometastases in Solid Tumours, *European Journal of Cancer* 36 (2000) 1681-1694, Mar. 2000, Elsevier Science Ltd.

Flatmark, Kjersti, et al., Immunomagnetic Detection of Micrometastatic Cells in Bone Marrow of Colorectal Cancer Patients, *Clinical Cancer Research*, vol. 8, 444-449, Feb. 2002.

Méthes, Gábor, et al., Quantitative Analysis of Disseminated Tumor Cells in the Bone Marrow by Automated Fluorescence Image Analysis, *Cytometry (Communications in Clinical Cytometry)*, 42:357-362 (2000, Wiley-Liss, Inc.

Werther, M., et al., The Use of the CELLection Kit in the Isolation of Carcinoma Cells from Mononuclear Cell Suspensions, *Journal of Immunological Methods*, 238 (2000) 133-141, 2000 Elsevier Science B.V.

Burchill, SA, et al., Comparison of the RNA-Amplification Based Methods RT-PCR and NASBA for the Detection of Circulating Tumour Cells, *2002Cancer Research Campaign, British Journal of Cancer* (2002) 86, 102-109.

\* cited by examiner

FIG. 7C
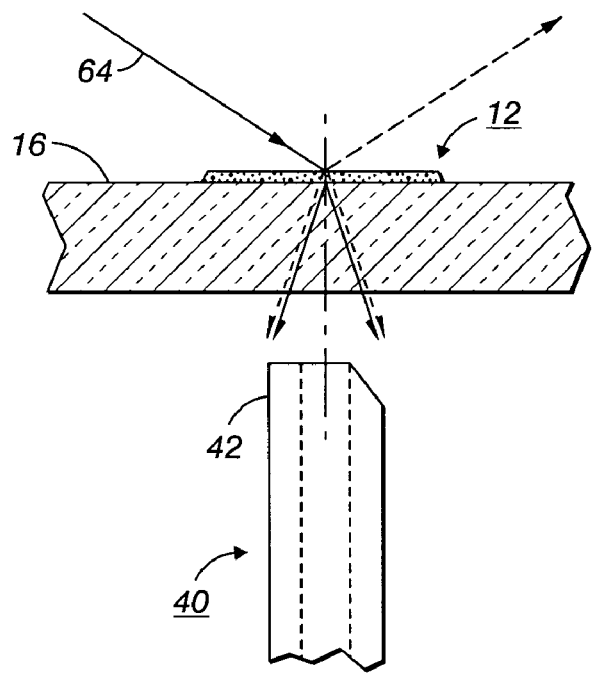
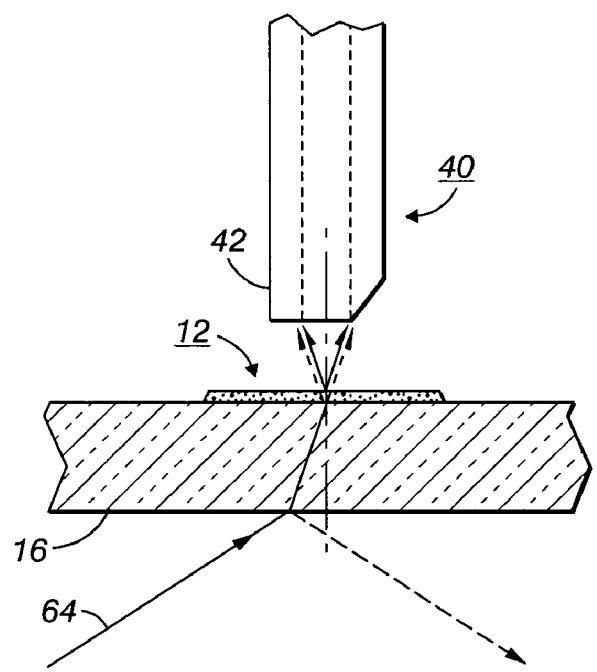
FIG. 7D

APPARATUS AND METHOD FOR DETECTING AND LOCATING RARE CELLS

CROSS REFERENCE

This is a continuation-in-part of U.S. Ser. No. 10/271,347, filed Oct. 15, 2002, now U.S. Pat. No. 7,113,624, incorporated herein in its entirety.

BACKGROUND OF THE INVENTION

The present invention relates to the imaging arts. It finds particular application in conjunction with low and high-density cell detection in blood smears, biological assays, and the like, and will be described with particular reference thereto. However, it is to be appreciated that the present invention will also find application in imaging other types of low-or high-density features on various substantially planar surfaces and samples, such as imaging semiconductor wafers, imaging particulate contaminants in fluids or thin solid films, and so forth, with such imaging finding specific uses in the printing arts, electronic arts, medical arts, and other scientific and engineering areas.

With particular attention to cell detection, it has been determined by the inventors that a beneficial aspect to which the present application may be applied is to scan a large number of cells, which has been considered to be in the range of 1 to 10 million cells. However, researchers and medical personnel are interested in being able to scan larger numbers of cells, such as up to 50 million or more cells, at a time. Thus, a system which can efficiently and quickly scan these large numbers of cells would be beneficial. Thereafter, the concepts of the application may be used to identify and/or locate either a small number of these cells, such as rare cells found in cancer, etc., or to be able to characterize each one of the scanned cells for use in diagnostic and/or research applications. As a general concept, the bloodstream of a living being primarily includes circulatory cells that move blood through the circulatory system, without becoming attached to other cells. However, circulatory systems also include non-circulating adherent type cells that have a tendency to adhere to markers added to the samples. For most cases, the cells being investigated are non-circulatory cells with characteristics different from circulatory cells. Once these cells are located, they may be investigated to identify their state, be counted, analyzed and/or made part of an immuno-assay (i.e., to look for proteins).

Clinical prenatal care benefits from directly accessing fetal tissues. In conventional amniocentesis, amniotic fluid surrounding the fetus is directly accessed and drawn. The amniotic fluid includes fetal cells that are extracted for study. To reduce risk to the fetus, ultrasound monitoring is typically performed during the amniocentesis to ensure that the probe needle does not contact or interfere with the fetus, and the amniocentesis procedure is performed by skilled clinical personnel. Nonetheless, amniocentesis is known to increase the risk of miscarriage with some statistics showing the risk at one in a hundred.

As an alternative to amniocentesis, rare fetal cells in the maternal bloodstream can be extracted. It is known in the prenatal medical arts that fetal cells cross the placental barrier and enter the maternal bloodstream. The concentration of fetal cells in the maternal bloodstream is typically on the order of one fetal cell for every one million maternal cells. Such "rare" fetal cells can be extracted by drawing maternal blood or by other fluid extraction. DNA analysis, fetal blood typing, or other clinical studies are performed on the rare fetal cells to provide information about the fetus.

Unlike amniocentesis, extraction of rare fetal cells from the maternal bloodstream is isolated from the fetus and the womb, and the extraction can be performed by a broad range of medical personnel authorized to draw blood. In this situation the risks attendant with amniocentesis is avoided.

While the above subject matter has referred to obtaining samples from the bloodstream, detection and locating cells of different bodily fluids, such as urine, bone marrow or others, may also be beneficial.

In the clinical oncology arts, it is recognized that tumors cells are typically present in small concentrations in a patient's bloodstream. In the case of deep malignant tumors which are inaccessible except by invasive surgery, as well as tumors at different stages of development, tumor cells extracted from blood or other body fluid provide a convenient and cost effective pathway for detecting a cancer, periodically monitoring cancer remission, and diagnosing a cancer type and/or stage and monitoring treatment. Rare cell analysis targeting timorous cells is a promising diagnostic and monitoring technique for many types of cancers, including breast, lung, colon, and prostate cancers. Another beneficial aspect of rare cell research is the potential for early cancer detection prior to the formation of tumors.

In these and other rare cell studies, a problem arises because the concentration of the rare cells in the blood or other body fluid is typically very low. In a typical rare cell study, blood is processed to remove cells that that are not needed. Then a fluorescent material is applied that attaches to antibodies, which in turn selectively attach to a cell surface or cellular protein of the rare cells. The cellular proteins may be membrane proteins or proteins within a cell, such as cytoplasm proteins. The antibodies may also attach to other types of molecules of the rare cell, as well as to DNA.

The fluorescent material may be a fluorescent marker dye or any other suitable material which will identify the cells of interest. A smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells, and up to fifty million or more, for a one-in-one-million rare cell concentration. Such a blood smear typically occupies an area of about 100 cm$^2$. It is to be understood, however, that this is simply one example and other numbers of cells may be required for statistical accuracy for a particular test or study. Other cell identifiers which are being used and investigated are quantum dots and nano-particle probes. Also, while a rare cell is mentioned as a one-in-one-million cell concentration, this is not intended to be limiting and is only given as an example of the rarity of the cells being sought. The concepts discussed herein are to be understood to be useful in higher or lower levels of cell concentration.

Turning to research applications, the scanning of a large number of cells and the characterization of each of the scanned cells may also have substantial benefits. For example, a hundred different patches, each containing 10,000 cells, maybe generated where each patch will receive a different protocol or process. Thereafter it may be useful to determine how each cell on a specific patch is affected by the protocol or process which it has undergone. One procedure of achieving such detection would be to apply a fluorescent material, and to identify those cells to which the material has become attached either to the cell's surface, cellular proteins or other portions of the cell.

A particular area of research which may benefit from the present concepts includes HIV research, where it is known the virus enters into a cell causing the cell to produce the viral protein on its membrane. However, the produced viral protein exists in very small amounts, and therefore it is difficult to detect affected cells with existing technology.

A number of cell detection methods and processes have been proposed. These include various types of automated microscopic imaging, such as described by Bauer et al. in "Reliable and Sensitive Analysis of Occult Bone Marrow Metastases Using Automated Cellular Imaging," *Clinical Cancer Researcher*, Vol. 6, 3552-3559, September 2000. By use of this technique, a scan rate of approximately 500,000 cells in eighteen minutes was obtained.

Another technique used for cell detection in the blood is the use of immunomagnetic cell enrichment in combination with digital microscopy. This technique is reported by Witzig et al. in "Detection of Circulating Cytokeratin-Positive Cells in the Blood of Breast Cancer Patients Using Immunomagnetic Enrichment and Digital Microscopy", *Clinical Cancer Researcher*, Vol. 8, 1085-1091, May 2002.

A proposed cancer detection technique uses reverse transcriptase polymerase chain reaction (RT-PCR) with some immunomagnetic isolation. A discussion of such a technique is, for example, set forth in the article by Ghossein et al. entitled "Molecular Detection and Characterization of Circulating Tumour Cells and Micrometastases in Solid Tumours," *European Journal of Cancer*, 36 (2000) 1681-1694. Another form of immunomagnetic detection is described by Flatmark et al. in the article, "Immunomagnetic Detection of Micrometastatic Cells in Bone Marrow of Colorectal Cancer Patients," *Clinical Cancer Researcher*, Vol. 8, 444-449, February 2002.

Accurate quantification of disseminated tumor cells is proposed to be obtained by using a fluorescence image analysis as disclosed by Mëhes et al. in the article entitled "Quantitative Analysis of Disseminated Tumor Cells in the Bone Marrow of Automated Fluorescence Image Analysis," in *Cytometry (Communications in Clinical Cytometry)*, 42:357-362 (2000). Another technique which enables a subsequent immunological characterization of isolated cells is obtained by the use of a immunomagnetic microbead isolation technique as discussed in the article by Werther et al., "The Use of the SELLection Kit™ in the Isolation of Carcinoma Cells from Mononuclear Cell Suppression," *Journal of Immunological Methods*, 238 (2000) 133-141.

Burchill et al. provides a review and comparison of several detection methods in "Comparison of the RNA-amplification Based Methods RT-PCR and NASBA for the Detection of Circulating Tumour Cells," *British Journal of Cancer*, (2002) 86, 102-109. Discussed are studies which suggest nucleic acid sequence-based amplification (NASBA) of targeted RNA may provide a robust manner of detecting cancer cells.

The above papers illustrate the wide range of research which is being undertaken in the are of rare cell detection and identification. In this regard, the ability to scan large numbers of cells at a high rate is considered a key aspect which increases the throughput of the testing processes. The processes described in the cited papers set forth a variety of cell detection and location techniques. It is considered to be valuable to provide a system which improves the speed, reliability and processing costs which may be achieved by the systems or processes cited in the above papers.

A cell detection technique which is noted in more specific detail is fluorescence in situ hybridization (FISH). This process uses fluorescent molecules to paint genes or chromosomes. The technique is particularly useful for gene mapping and for identifying chromosomal abnormalities. In the FISH process, short sequences of single-stranded DNA, called probes, are prepared and which are complementary to the DNA sequences which are to be painted and examined. These probes hybridize, or bind, to a complementary DNA, and as they are labeled with a fluorescent tag, it permits a researcher to identify the location of sequences of the DNA. The FISH technique may be performed on non-dividing cells.

Another process of cell detection is flow cytometry (FC), which is a means of measuring certain physical and chemical characteristics of cells or particles as they travel in suspension past a sensing point. Ideally the cells travel past the sensing point one by one. However, significant obstacles exist to achieving this ideal performance, and in practice a statistically relevant number of cells are not detected due to the cells bunching or clumping together, making it not possible to identify each cell individually. In operation a light source emits light to collection optics, and electronics with a computer translates signals to data. Many flow cytometers have the ability to sort, or physically separate particles of interest, from a sample.

Another cytometry process is known as laser scanning cytometry (LSC). In this system, data is collected by rastering a laser beam within the limited field of view (FOV) of a microscope. With laser rastering, the excitation is intense and in a single wavelength, which permits a differentiation between dyes responsive at distinct wavelengths. This method provides equivalent data of a flow cytometer, but is a slide based system. It permits light scatter and fluorescence, but also records the position of each measurement. By this design, cells of interest can be relocated, visualized, restained, remeasured and photographed.

While it is appreciated that increasing the speed at which cells are scanned is a valuable characteristic, a problem with these existing cell analysis techniques is the use of conventional technology which have relatively small fields of view (FOV), such as microscopes. To overcome the FOV limitation, cell analyses often employ automated high-speed scanning which however produces substantial undesirable acceleration forces on the scanned stage.

Another problem in cell studies, for both high and low density situations, is that the fluorescence intensity produced by treated cells is low, around 1000-2000 flours (fluorescent molecules). A high numerical aperture for the light-collecting aperture is preferred in the optical analysis system to provide good light collection.

Yet another problem in the cell studies is resolution. For example, if a cell has a diameter of about ten microns, the optics for the cell analysis preferably provides a resolution of this order. However, achieving high resolution typically requires a reduced field of view and consequently results in a decreased scanning speed and increased required sampling time.

The present invention contemplates a new and improved apparatus and method which overcomes the above-referenced problems and others.

BRIEF DESCRIPTION OF THE INVENTION

In accordance with one aspect of the present application, an imager for imaging a sample is disclosed. An imager stage supports the sample. A fiber optic bundle has a proximate bundle end of first fiber ends arranged to define an input aperture collecting light from the sample on the imager stage. The fiber optic bundle further has a distal bundle end of second fiber ends arranged to define an output aperture shaped differently from the input aperture and disposed away from the imager stage. A scanning radiation source is arranged in fixed relative position to the input aperture. The scanning radiation source scans a radiation beam on the sample within a viewing area of the input aperture. The radiation beam interacts with the sample to produce a light signal that is reflected, scattered, transmitted, re-emitted, or otherwise collected and received by the input aperture and transmitted via the fiber optic bundle to the output aperture. The scanning radiation source rasters the radiation beam over a selected area of the sample. A photodetector is arranged to detect the light signal at the distal bundle end, and a processor processes the detected light signals.

In accordance with another aspect of the present invention, an imaging method is provided. A radiation beam is swept along a linear path on a first portion of a sample. Light produced by the beam interaction with the first portion of the sample is collected using at least one proximate element of an array of fiber optic ends. The collected light is transmitted along a fiber associated with the at least one proximate element. The fiber channels the collected light to a selected output region. A largest spatial dimension of the output region is substantially smaller than a largest spatial dimension of the array of fiber optic proximal ends. The collected light is detected at the selected output region. The sample is moved generally perpendicularly to the linear path of the radiation beam sweeping. The moving cooperates with the sweeping to produce a raster pattern of the radiation beam on the sample. Following investigation of the first portion of the sample, the sample is moved such that a second portion of the sample is positioned for investigation. The sweeping, moving, and detecting are coordinated to generate an array of picture elements representative of at least a portion of the first portion and second portion of the sample.

In accordance with yet another aspect of the present invention, an apparatus and method is disclosed for identifying rare cells in a biological smear. The rare cells emit a characteristic luminescence responsive to exposure to an excitation radiation. A translating stage is able to translate the biological smear in a first and a second direction. A fiber optic bundle includes a plurality of fibers each having a first end and a second end. The first ends are arranged to define a generally rectangular receiving aperture having a large aspect ratio whose long dimension is perpendicular to the first direction. The second ends are arranged to define an output aperture having a compact shape. A radiation source linearly sweeps an excitation radiation beam across the first portion of the biological smear with a sweep direction perpendicular to the first direction. An interaction region of the radiation source and the first portion of the biological smear is arranged relative to the receiving aperture such that characteristic luminescence produced in the interaction region is collected by the receiving aperture. A photodetector is arranged to detect the collected characteristic luminescence at the output aperture. A controller controls the translation of the imager stage and the sweeping of the radiation source to raster the excitation radiation beam across the first portion of the biological smear to identify rare cells in the first portion of the biological smear based upon the characteristic luminescence detected during the rastering. The controller further controls translation of the translation stage in a second direction to place a second portion of the biological smear in a position where the radiation source linearly sweeps the excitation radiation beam across the second portion of the biological smear with a sweep direction perpendicular to the first direction. An interaction region of the radiation source and the second portion of the biological smear are arranged relative to the receiving aperture such that characteristic luminescence produced in the interaction region is collected by the receiving aperture. The photodetector is arranged to detect the collected characteristic luminescence at the output aperture of the second portion.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIGS. 7A-7D reflect four permutations of the relationship between the fiber bundle head, the slide containing a sample, and the excitation beam path.

DETAILED DESCRIPTION OF THE INVENTION

Figure 1:
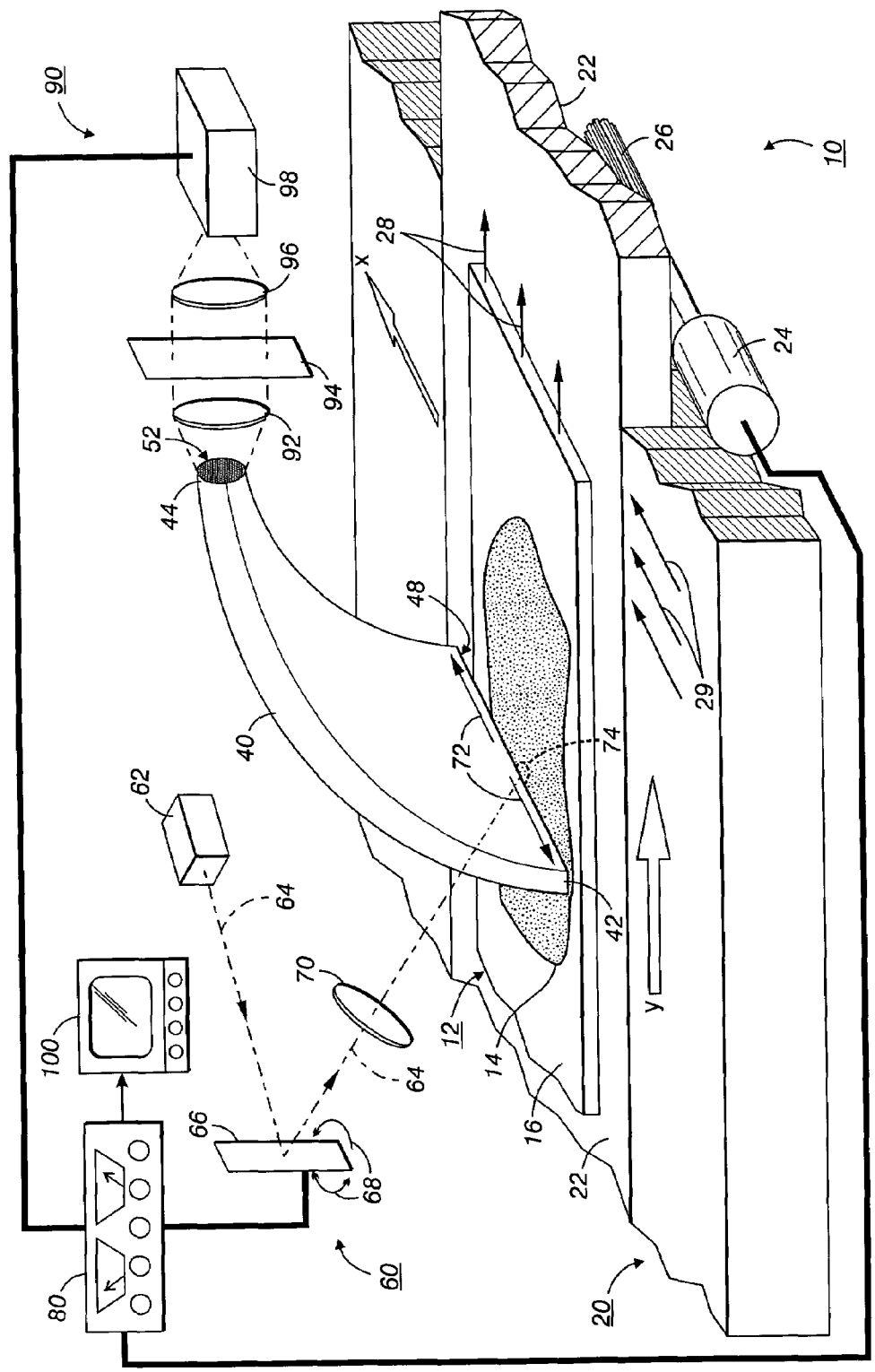
FIG. 1 shows a perspective view of an imaging apparatus formed in accordance with a preferred embodiment of the invention.

With reference to FIG. 1, an imaging apparatus or imager 10 examines a sample 12 such as a biological smear 14 disposed on at least a portion of a surface of a slide 16. Imaging apparatus or imager 10, as expanded upon below, is designed for detection of minute or microscopic material. It is to be appreciated that while the following discussion describes imager 10 in connection with specific material of certain sizes, it is not intended to be limited to use only in connection with these materials and these sizes, but rather is considered applicable to all materials and sizes, which would be detectable by the described device and method. Further, the imaging apparatus and imager are intended to include all appropriate image forming devices, including but not limited to a microscope and digital image.

The described system is intended to assist in the search for tumor or fetal cells, as well as other cells which may be detected in the blood stream. Particularly, it is believed cells from organs and tissues of the body, such as but not limited to kidney, liver or brain cells, may be shed into the bloodstream. It has been proposed that detecting existence of such cells in the bloodstream may permit early detection of existing or potential diseases. Therefore, why these cells, as well as others, are in the bloodstream and what this means is being studied with great interest. Thus, it is theorized the mere presence of the cells may indicate a health related issue. For example, if nerve cells are in the bloodstream, this may indicate a neurological problem. Alternatively, the fact certain cells are found in the bloodstream may not in itself indicate a problem, but being able to identify and locate the cells will permit investigation to determine the state of the cells. In all cases, whether it is determined that the finding of unexpected cells within the bloodstream are a link to diseases or provide other physiological information, detection and locating of the cells are initial steps. Further, as these cells commonly occur in very low levels, a high-speed detection mechanism and/or process greatly enhances cell investigations. Thus, when the existence of cells in the bloodstream do correlate to the presence of a disease or other physiological status, a high-speed detection device would be highly beneficial in locating the cells.

For instance, when it is believed bacteria may be in a patient's bloodstream, a common medical process is to order a culture of the patient's blood. Developing the culture may take from several hours to days, which is a significant drawback in time-critical situations, such as when the patient runs the risk of entering a septic shock state. Therefore, the detection of bacteria in blood with a very fast process would obviously have great value.

As is known in the art, for cell studies the sample 12 is suitably prepared by drawing a sample of a biological fluid such as, but not limited to, blood or parts of blood from a subject. In a preferred embodiment, the sample is a monolayer of cells. The fluid sample is treated with a fluorescent material, such as but not limited to a marker dye, that selectively bonds to different kinds of biological molecules, which may be on the surface or inside the cell, such as proteins, nucleic acids or other molecules. Suitable markers are known in the art for marking a number of different cell types of clinical interest, including selected cancer cell types, fetal cells, or other appropriate cells to be considered. Work is also being undertaken to develop marking materials for numerous other cells such as brain cells, liver cells, as well as bacteria cells, among others. The material preferably emits a characteristic output, such as a fluorescence or a phosphorescence, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths. While dyes are the predominant tagging process, other techniques exist including the use of markers known as quantum dots and DNA nano-particle probes.

The treated biological fluid is smeared onto a transparent slide using known techniques. In one suitable technique, a drop of the fluid is applied to the transparent slide 16, and an edge of a second transparent slide or other well-defined, clean edge is used to spread the drop across the slide 16. In another suitable technique, the fluid is applied while the slide 16 is being rotated by a spinner, so that centrifugal forces cause the fluid to smear out substantially uniformly over the slide 16. Other methods for preparing the biological smear can be substituted for the exemplary techniques.

The smear size will depend on the implementation, however, as an example, in one situation for a rare cell concentration of about one rare cell of interest per one million cells in the biological fluid, the smear 14 might contain one million or about 10 million to 50 million or more cells and occupy an area of about 100 cm$^2$ or greater. Of course, larger or smaller smears can be prepared which are suitable for the anticipated concentration of cells in the sample and the desired minimum measurable cell concentration.

The sample 12 is mounted on an imager translation stage 20 (shown in part) which includes a linearly translatable track 22 that supports the sample 12. A motor 24 connects with the track 22 via gearing 26 to translate the track 22 and the supported sample 12 along a y-direction (indicated by arrows 28) and a x-direction (indicated by arrows 29). Although translation stage 20 driven by a rotary motor 24 is shown in FIG. 1, it is also contemplated to employ other types of mechanical driving devices. Furthermore, other types of sample movement such as sample rotation are also contemplated.

Figure 2:
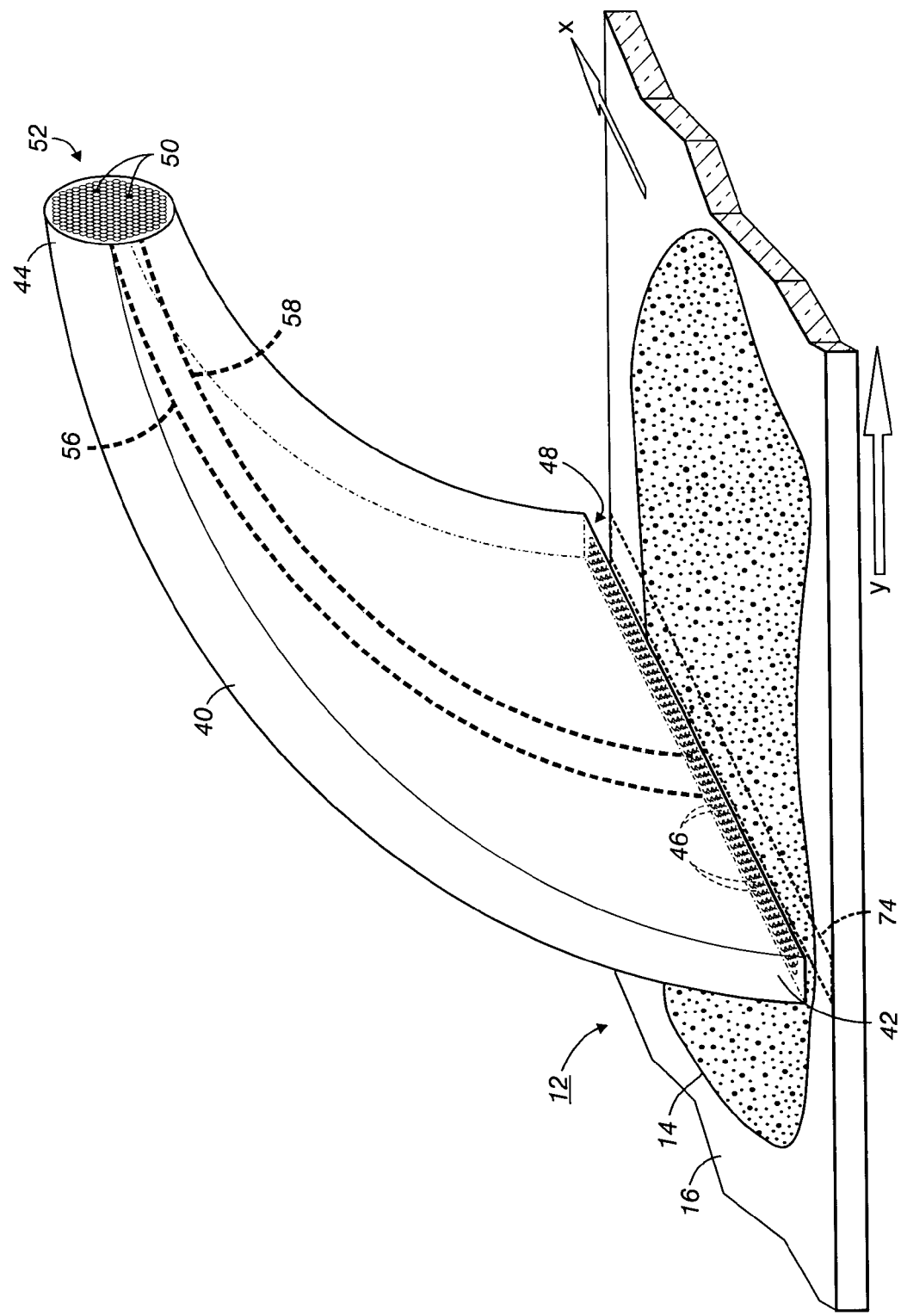
FIG. 2 shows an enlarged perspective view of the morphed fiber optic bundle of the imaging apparatus of FIG. 1 in relation to the sample.
Figure 3:
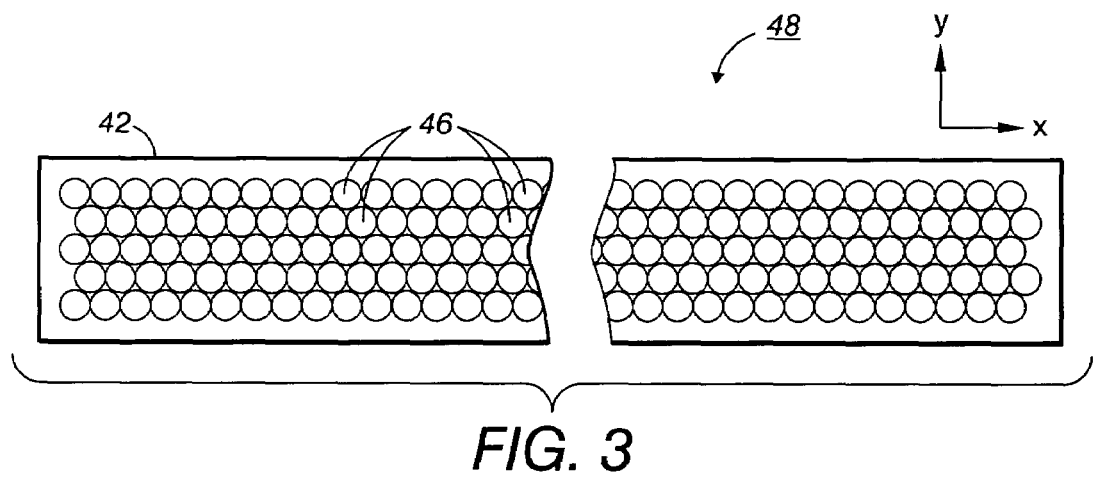
FIG. 3 shows an enlarged end view of the first end that defines the input aperture of the morphed fiber optic bundle of the apparatus of FIG. 1.

With continuing reference to FIG. 1 and with further reference to FIGS. 2 and 3, a fiber optic bundle 40 includes a first end 42 that is proximate to the sample 12, and a second end 44 that is distal from the sample 12. The first end 42 includes a plurality of first fiber ends 46 arranged substantially parallel to one another in an arrangement that defines a generally linear or high-aspect-ratio rectangular input aperture 48 (best seen schematically in FIG. 3) with a long dimension aligned with the x-direction. The input aperture 48 preferably includes a large number of first fiber ends 46, i.e. thousands of fiber ends. In one suitable embodiment, 40,000 fibers each having an approximately 50 micron diameter are arranged into a 40 fiber-by-1000 fiber array to define the input aperture 48 with a long dimension of approximately 5 cm and a short dimension of about 0.2 cm corresponding to a 25:1 aspect ratio. The first fiber ends 46 can be arranged in a regular pattern, as shown in FIG. 3. Alternatively, the first fiber ends can be arranged in an irregular or non-periodic array and may have diameters which are greater or less than 50 microns. Although generally round fiber ends are shown, it is also contemplated to employ fibers with oval, square, hexagonal, or other cross-sectional shapes. The first fiber ends 46 are oriented substantially perpendicular to the plane of the biological smear 14 so as to view the smear 14.

The optical fiber bundle 40 "morphs" or changes cross-sectional dimensions and shape between the first end 42 to the second end 44 such that the second end 44 includes a plurality of second fiber ends 50 (best seen schematically in FIG. 2) that define a compact, generally circular output aperture 52. Preferably, there is a one-to-one correspondence between the first fiber ends 46 and the second fiber ends 50, and each first fiber end connects with a second fiber end by an individual, distinct fiber having its own waveguiding cladding. Alternatively, each fiber can include only a light-transmissive fiber core, and an ambient/core interface functions to waveguide the light. Other optical fiber types can also be used, such fibers being well known in the art and typically formed of glass, plastic, or other light-transmissive materials by extrusion methods. In FIG. 2, the paths of two exemplary individual, distinct fibers 56, 58 are indicated as dotted lines. The morphed shape of the fiber bundle 40 from an extended, generally linear first end 42 to a compact, generally circular second end 44 is preferably formed by varying a spatial arrangement of the fibers of the optical fiber bundle 40 in a continuous fashion. For the exemplary 40,000 fiber embodiment with each fiber having a 50 micron diameter, the generally circular output aperture 52 has a circular diameter of about 1.3 cm.

It is particularly pointed out that the spatial relationship between the first fiber ends 46 and the second fiber ends 50 is generally arbitrary. For example, in FIG. 2 the fibers 56, 58 run from approximately the same position in the input aperture 48. However, the fiber 56 terminates near a top of the output aperture 52, while the fiber 58 terminates near a middle of the output aperture 52. Although for convenience in arranging the fibers it is contemplated to arrange the first and second fiber ends 46, 50 in the respective apertures 48, 52 with a selected correspondence relative to one another, the fiber ends 46, 50 can instead have a generally uncorrelated and arbitrary relationship therebetween. Morphed fiber optic bundles similar to the fiber optic bundle 40 are known and used in the optical arts for other applications such as transforming focused light into a linear illumination pattern, and for coupling a light beam into a linear slit of a monochromator or spectrometer.

To obtain good light transmission, the fiber optic bundle 40 preferably has a high fiber packing factor, for example, fiber optic bundle 40 has a packing factor of about 0.80 or higher. Other factors influencing the light transmission include the polishing or light transmission properties of the tips of the first and second fiber ends 46, 50, the absorption per unit length of the fibers 56, 58, and the overall length of the fibers 56, 58. Fiber bending losses are preferably reduced by avoiding sharp bends of the fiber optic bundle 40. For example, as seen in FIGS. 1 and 2, the difference in orientation of the input aperture 48 and the output aperture 52 is achieved by a gradual bend in the optical fiber bundle 40.

Figure 4:
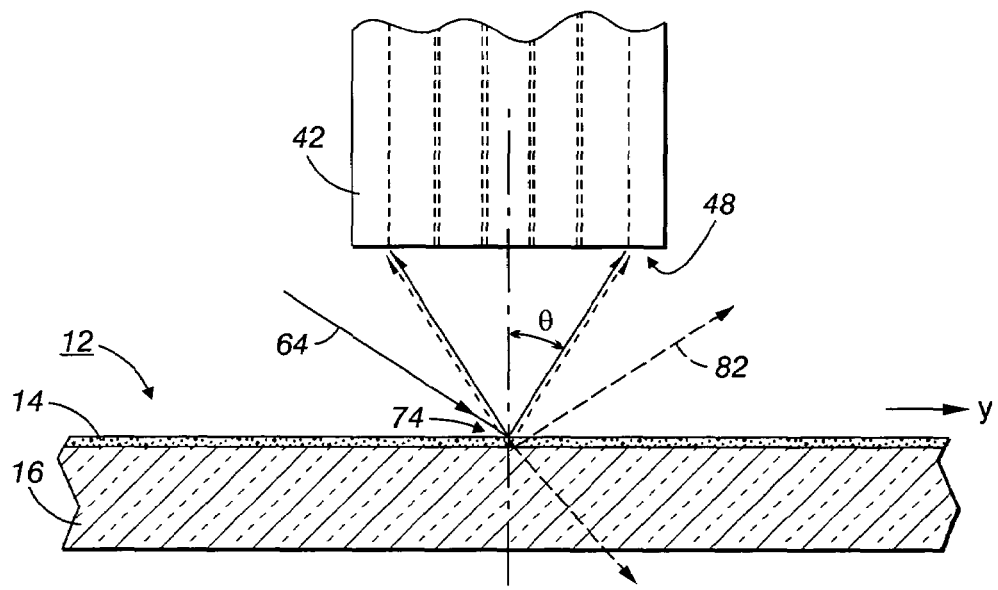
FIG. 4 shows a side view of the imaging apparatus of FIG. 1 centered on the first end of the morphed fiber optic bundle.

With continuing reference to FIGS. 1-3 and with further reference to FIG. 4, a scanning radiation (light) source 60 in a suitable embodiment includes a laser 62 that produces excitation light (radiation beam) 64 at a wavelength or wavelength range selected to excite the material used in marking the biological smear 14. The excitation light 64 is angularly scanned by a galvanometer 66 that has a reflective surface that rotates (indicated by curved arrows 68) responsive to an electrical input. An optional focusing lens 70 focuses the angularly scanned excitation light 64 onto the sample 12, and more particularly onto the biological smear 14. The angular scanning produced by the galvanometer 66 translates into a linear sweeping or fast scanning (indicated by arrows 72) of the excitation light on the biological smear 14 along a linear trajectory 74 arranged below the input aperture 48 and parallel to the long dimension of the input aperture 48. That is, using the coordinate system of FIG. 1 the linear trajectory 74 is parallel to the x-direction. In a suitable embodiment, the trajectory 74 is disposed on the biological smear 14 about one millimeter below the input aperture 48, although other distances will be appropriate dependant upon devices and the environment in which these concepts are implemented.

For cell studies, the excitation radiation 64 preferably produces a spot size on the biological smear 14 which substantially comports with a size of the cells, which may vary in size but are typically about one to thirty microns in size. To obtain such narrow beam focusing, the focusing lens 70 is typically included.

Those skilled in the art can make other suitable changes and substitutions in scanning radiation or light source 60 to accommodate specific applications. For example, the laser 62 can be replaced by an incandescent light source, light emitting diode (LED), or the like. The galvanometer 66 can be replaced by another optical scanning device, such as a polygon laser scanner similar to a type commonly employed in laser printers. The polygon laser scanner advantageously scans the beam more rapidly than the galvanometer 66. Furthermore, the scanning radiation or light source 60 shown in FIG. 1 can be replaced by a scanning x-ray source or a scanning electron beam employing beam deflectors. In the latter embodiment, the electron beam path is suitably enclosed in a vacuum environment.

With continuing reference to FIGS. 1-4, an electronic control unit 80 communicates with the galvanometer 66 and the translation stage 20 to coordinate the linear sweeping or scanning 72 of the radiation beam 64 along the trajectory 74 and the linear translation 28 of the sample 12 to effectuate a rastering of the radiation beam 64 across a selected area of the sample which is bounded in the x-direction by the smaller of a span of the trajectory 74 and the long dimension of the input aperture 42. Preferably, the span of the trajectory 74 substantially comports with the long dimension of the input aperture 42.

As best seen in FIG. 4, the excitation radiation beam 64 is incident upon the biological smear 14 at an oblique angle which is larger than a collection angle $\theta$ of the input aperture 42. The collection angle $\theta$ depends upon a short dimension of the input aperture 42, the distance between the input aperture 42 and the biological smear 14, and the light collecting characteristics of the first fiber ends 46. The latter is suitably characterized by a numerical aperture of the fiber ends. As is known in the art, an optical fiber end typically has a large numerical aperture corresponding to a large light collection angle which is particularly advantageous for collecting the typically weak characteristic luminescence of the cells. In a suitable embodiment, the radiation beam 64 impinges upon the sample 12 at 30°-90°, and preferably about 60° off the normal.

Because the incidence angle of the radiation beam 64 is larger than the collection angle $\theta$ of the input aperture 42, specularly reflected radiation 82 is not collected by the input aperture 42. However, the characteristic luminescence produced by the treated cells generally emits uniformly in all spatial directions, i.e. each treated cell corresponds to a point light source. Hence, a substantial portion of the characteristic luminescence is collected by the input aperture 42 due to its close proximity to and alignment with the radiation beam trajectory 74 on the biological smear 14 as well as the large numerical aperture of the first fiber ends 46. The collected light enters the first fiber ends 46, transmits along the individual fibers, e.g. the fibers 56, 58 shown in FIG. 2, and exits the optical fiber bundle 40 at second fiber ends 50 that correspond to the collecting first fiber ends 46.

It will be appreciated that the characteristic luminescence produced by a particular cell will not generally be collected by all or even most of the first fiber ends 46. Rather, only one or a few of the first fiber ends 46 which are closely proximate to the cell will collect the characteristic luminescence therefrom. In an exemplary embodiment, the radiation spot size is about 10-15 microns corresponding to a similarly sized cell, while each first fiber end 46 has a diameter of about 50 microns. Hence, only one or a few fibers may be needed to view and collect the characteristic luminescence for any given position of the sweeping radiation beam 64.

However, because at the second end 44 of the fiber bundle 40 the second fiber ends 50 are arranged to define the compact, output aperture 52, the characteristic luminescence emanates from a small region of space corresponding to the output aperture 52 regardless of which of the first fiber ends 46 collected the characteristic luminescence. As the excitation beam 64 sweeps along its trajectory 74 parallel to and typically below the input aperture 48, the proximate one or few of the first fiber ends 46 collect the characteristic luminescence, which is channeled by the fiber optic bundle 40 to the compact output aperture 52.

In the arrangement of FIG. 1, the scanning radiation source 60 and the input aperture 48 are arranged in fixed relative position, the galvanometer 66 provides a linear sweeping of the excitation beam 64 along the x-direction, and the sample 12 is moved by the translation stage 20 linearly along a y-direction to effectuate a two dimensional rastering. However, other rastering arrangements are also contemplated. In another suitable rastering arrangement, the input aperture has a smaller aspect ratio, i.e. a larger short dimension, such that the aperture spans the selected imaging area in both the x- and the y-directions. The scanning radiation source performs two dimensional rastering in both the x- and y-directions, while the sample remains stationary on the translation stage.

In yet another suitable rastering arrangement, the translation stage provides a rotational sample motion about a rotational axis normal to the scanned sample surface, and the input aperture has a generally linear shape, i.e. large aspect ratio, with its long dimension extending radially away from the rotational axis. The radiation beam sweeps linearly along the linear input aperture while the sample rotates to effectuate a rotational two-dimensional scanning.

In any of these rastering arrangements, the spatially distributed input aperture collects the characteristic luminescence using one or a few first fiber ends, and transmits the collected light to a compact second aperture via a morphed fiber optic bundle. As the rastering progresses, different first fiber ends perform the light collecting, but the light is continually channeled to a common compact output aperture for detection.

With reference to FIG. 1, a suitable signal detector 90 is arranged to detect the collected characteristic luminescence emanating from the output aperture 52. A first lens 92 substantially collimates the light. A light, such as but not limited to a laser light, blocking filter 94 is optionally provided to remove scattered laser light from the collected light. Although as shown in FIG. 4 the radiation beam 64 is preferably arranged so that reflected radiation 82 is not collected by the input aperture 48, typically some of the radiation beam 64 will be scattered by the sample 12 and collected by the input aperture 48. Because of the typically low intensity of the characteristic luminescence from the cells, even the collected scattered laser light can substantially interfere with signal detection.

In one suitable embodiment, the blocking filter 94 is an interference filter with a reflectance peak coinciding with a center wavelength of the radiation beam 64 is employed. As is known in the art, optical interference filters have a rejection ratio that is strongly dependent upon the angle of incidence of the light. An exemplary interference filter used in one actually constructed embodiment exhibits a $10^6:1$ or greater rejection ratio for light incident within $\pm 14°$ of normal incidence. In this constructed embodiment, the first lens 92 includes a lens combination, designed using known optical design methods, that collimates light emanating from the output aperture 52 to within a $\pm 10°$ angular divergence.

With continuing reference to FIG. 1, a second lens 96 focuses the collimated collected light onto a photodetector arrangement 98. By combining the compact output aperture 52 with focusing optics 92, 96, photodetector 98, which may be a single photodetector, provides signal detection for the spatially distributed linear input aperture 48. Because of the typically low collected characteristic luminescence intensities produced by treated cells, the photodetector 98 is preferably a photomultiplier tube. As is known in the art, a photomultiplier tube provides substantial signal gain through cascade multiplication of electrons in a multi-stage high-voltage cathode. To further improve the signal-to-noise ratio, the optical path of the signal detector 90 is preferably enclosed to substantially reduce noise due to stray light.

Those skilled in the art can suitably modify the signal detector 90 by addition, removal, or substitution of components to adapt it to specific imaging situations. For applications providing an alternate signal-to-noise characteristics, a photodiode can be used for the photodetector 98. Similarly, the single photodetector 98 and multiple focusing elements 92, 96 can be replaced by a photodetector array having an area that comports with an area of the output aperture 52.

In contrast, it is to be appreciated that for certain applications, such as but not limited to microscope applications, not involving luminescence, i.e., collection of reflected, transmitted or scattered radiation from the scanning spot, blocking filter 94 is optionally omitted. When blocking filter 94 is omitted and the output aperture 52 has a small enough area, the optics 92, 96 may be omitted entirely while retaining the use of a single photodetector that substantially spans the small output aperture area. Alternatively, in luminescence applications, optics 92 and 96 may also be omitted when the blocking filter 94 embodied as an interference or reflection filter, is located on the slide, when the fiber bundles themselves are made of an absorptive filter material, or the slide is the absorptive blocking filter.

In one embodiment, the blocking filter, which is an interference filter, may be an interference filter set such as developed by Chroma Technologies Corporation of Brattleboro, Vt. These filter sets are commonly used for fluorescence microscopes (a dichroic mirror long pass filter and an emitter ban pass filter) which is typically used to divert and exclude laser light from a signal path. The dichroic mirror is placed at 45° and is properly used to deflect the excitation beam (i.e., laser light) out of the path at right angles. The emitter filter is properly placed normal to the path of the excitation beam after the mirror filter and is typically used to further block the excitation beam, passing the fluorescence signal onto the detector.

In other embodiments, absorptive filters, such as Schott OG515 (from Schott Glass Technologies, Inc. of Duryea, Pa., may be added to further exclude the excitation beam (i.e., laser light). It needs to be appreciated the foregoing simply provides details to examples of filters which may be used, and this discussion is not intended to limit the disclosures to these particular filters, but rather, when the filter design is incorporated, the present application is intended to be used with any appropriate filter design.

With continuing reference to FIG. 1, the electronic control unit 80 communicates with the galvanometer 66 and the translation microscope stage 20 to raster the radiation beam 64 across the sample. Characteristic luminescence produced by interaction of the radiation beam 64 with treated cells in the biological smear 14 is collected by the input aperture 48, channeled to the output aperture 52 by the optical fiber bundle 40, and detected by the signal detector 90. The electronic control unit 80 receives the detected signal from the photodetector 98, and correlates the detected signal with positional coordinates of the radiation beam 64 on the sample 12.

In particular, the electronic control unit 80 identifies a beam sweep position as a first coordinate in the x-direction, and a position of the translation stage 20 as a second orthogonal coordinate in the y-direction, to spatially map out the collected characteristic luminescence intensity as a function of position on the sample 12. The x- and y-coordinates can be inferred from the laser scan velocity and stage translation velocities, respectively. Alternately, registration marks on the sample media can be included to identify absolute x,y position information. In addition, one or both of the galvanometer 66 and the translation stage 20 can include a position sensor which is read by the electronic control unit 80 to ascertain the coordinates of the radiation beam 64 on the sample. The electronic control unit 80 suitably formats the detected signal and spatial coordinates information and stores the information in an internal memory, writes the information to a non-volatile storage medium such as a magnetic or optical disk, formats and displays an image representation including an array of picture elements with coordinates mapped to the spatial coordinates information and an intensity or color mapped to the detected signal intensity on a display 100, or the like.

Those skilled in the art can modify the electronic control unit 80 and associated devices such as the display 100 for specific applications. In a preferred embodiment, a personal computer performs the control and data collection functions of the electronic control unit 80 and includes a display and printer for displaying the image representation, and further includes a user interface for user input of a selected imaging area and other imaging setup information, a hard disk for storing the formatted detected signal and spatial coordinates information, and an optional network connection for electronically transmitting the information to other devices.

As previously discussed, during the scanning operations, interaction of the spot generated by the laser beam with cells which have been tagged in a sample, will cause those tags to emit fluorescent light. Commonly, these tags will be clustered within the cells and will generate high-intensity pixels when the cells that enter a fluorescent state reemit upon scanning by the radiation spot. For the following discussion, the detected unknown cluster of tags is described as an "image event" to which further investigation is warranted. The size of the radiation spot defines the resolution of the imaging device.

Pixel data—of a particular image event—used for imaging purposes, may be acquired, in one embodiment, with an image pixel width equal to a width of the spot in the fast scan direction, and an image pixel height equal to the scan pitch, in the process direction. The fast scan direction corresponds to the linear sweeping or scanning direction 72 of FIG. 1, and the process direction corresponds to the movement of sample 12 in direction 28 during the scanning process. The scan pitch is the distance between scans. In a situation, where an embodiment of the radiation beam 64 impinging on the sample 12 is preferably about 60° off the normal, it would be expected that the corresponding radiation spot is elongated in the process direction by a factor of about 1/cos (60°)=2, and therefore would determine the scan pitch to be twice the fast scan pixel width.

Therefore, the resultant pixel size would be rectangular, with its process direction dimension twice that of the fast scan dimension. Under this design, fast processing speeds would be obtained since the scans in the process direction would be farther apart than that in the fast scan direction, providing a higher throughput. An issue with this data acquisition mode is that in creating pixels that are not square, the acquired pixels will not stack squarely into an image with a commonly used aspect ratio. As an alternative, pixel acquisition mode may be undertaken with both the image pixel width (i.e., in the fast scan) and the scan pitch (i.e., in the process direction) equal to the fast scan width of the spot. The resultant pixel size would be square. This acquisition process provides images compatible with existing industry image viewers that default to the expectation of square pixels, and therefore could be applied to systems which have a commonly used aspect ratio.

Determining whether pixel acquisition should be either square or rectangular pixels, will affect the resulting shape information for image processing. For example, a particular image event may have a pixel shape of either 2×2 (fast× slow) pixels, or 2×3 pixels, depending on the acquisition mode pixel aspect ratio.

Another parameter that affects image processing is the phase of the image event. For example, if a 10 micron structure is in-phase with both the operation in the scan pitch (process direction) and fast scan width (fast scan), an image event would produce a 1×1=1 pixel. If the same 10 micron structure were 180° out of phase with the scan pitch, then part of the structure would be detected during two scan lines, producing two pixels, one from each scan line (i.e., 1×2=2) pixels. In the same manner, if the 10 micron structure were 180° out of phase with the fast scan pitch, then part of the structure would be detected during two pixel acquisition times producing two pixels in the fast scan direction (i.e., 2×1=2 pixels). Combining both these situations would result in a 2×2=4 pixels image event for the 10 micron structure.

Stated another way, a cluster of tags may be seen on two separate clock data acquisition events during a fast scan process. For example, if the radiation spot is in a first position, and a measurement is made, then the spot moves to a second location further along in the fast scanning process, and a second measurement is made, there may be some overlap of the image event with the spot, i. e., signals from a single image event would be detected at different clock events. Similarly, when out of phase with the process direction, signals from a single image event would be detected from two separate scan lines.

As another example, if the spot were oval (e.g., long in the process direction), signals from a single image event could be detected from three or more separate scan lines. A first scan may detect an upper edge of that image event, the middle scan, the middle portion, and the third scan could detect the lower end of the image event. In this process, the signal may be a 2×3 pixel image.

As described above, image data is acquired dependant on the speed and operation of the scanning in the fast scan and process direction, and also in consideration of the radiation spot size, as well as the angle of incidence of the spot.

When working with such small structures, noise—such as dirt or dust particles, or miscellaneous cells—may be found on the sample 12, and will have an effect on the acquired image information. Specifically, the imager 10 may accumulate image data irrelevant to the identification of rare cells. At times this noise may be considered as "false positives." It is desirable to eliminate this noise (including false positives) during image acquisition and processing. Therefore, filtering procedures may be implemented via electronic control unit 80 and/or other elements of the system 10 to eliminate information not related to rare cells. The filtering techniques may use various characteristics of an image event to perform the filtering operations, including the number of pixels, intensity, phase and shape of the image event under consideration.

In one embodiment, an image event may be classified as a non-rare cell or a rare cell image event by counting the number of pixels of the image event under investigation. Knowing approximate sizes of rare cell tag clusters under investigation, a range can be set to filter out those image events having either a number of pixels less than or greater than the prescribed range. For instance, if the range of rare cells would be known to correlate to a number of pixels in a range of 1 to 12, then image events having a pixel range greater than 12, would be eliminated in a filtering operation.

In another filtering embodiment, the shape of an image event is used to filter non-relevant information. Specifically, in many instances an image event correlating to a rare cell or cluster of rare cells would have a known shape corresponding to the rare cells being imaged, and blurred by the impulse response of the radiation spot. If the detected shape is other than expected for the pertinent rare cell and/or clusters of rare cells, this would indicate the detected image event is noise such as a dust or dirt particle or other irrelevant signal from the sample. To assist in the filtering in this arrangement, known pattern matching software may be implemented in imaging system 10. In this filtering operation, it would be expected not to see an image event that had a finer structure than the spots own resolution size. Particularly, the image event would not be smaller than the spot size, although the structure itself may be smaller.

Still a further filtering process which may be used to identify rare cell image events from non-rare cell image events is by tracking the intensity of the image event under investigation. For example, in the discussion related to the phase of the 10 micron structure, it would be expected that a higher intensity would be detected for rare cell image events that were in phase with the pixel acquisition phase, and would also provide fewer pixels. Out of phase image events would have their energy shared with several neighboring pixels, thereby providing a smaller intensity per pixel, but more pixels. In addition, in some non-specific binding of tags on cells, i.e., cells not related to the rare cells, may produce image events but these would have a lower intensity than the expected intensity from rare cell binding clusters.

The foregoing describes filtering techniques to determine rare cell events from the image events detected by the imaging system through the use of comparisons of various characteristics either alone or in combination, including the size, intensity, phase or shape of an acquired imaging event.

The detected signal, generated images and spatial coordinates information can be used in various ways. For monitoring a cancer remission state in a patient, a count of rare cells corresponding to the monitored cancer type in a standard smear area, e.g. a 5 cm×20 cm standard smear, can provide a useful figure of merit for the monitoring. For medical diagnostic applications, the identified rare cells are preferably extracted using known methods, and suitable DNA analysis or other diagnostic clinical testing is performed on the extracted rare cells.

Figure 5:
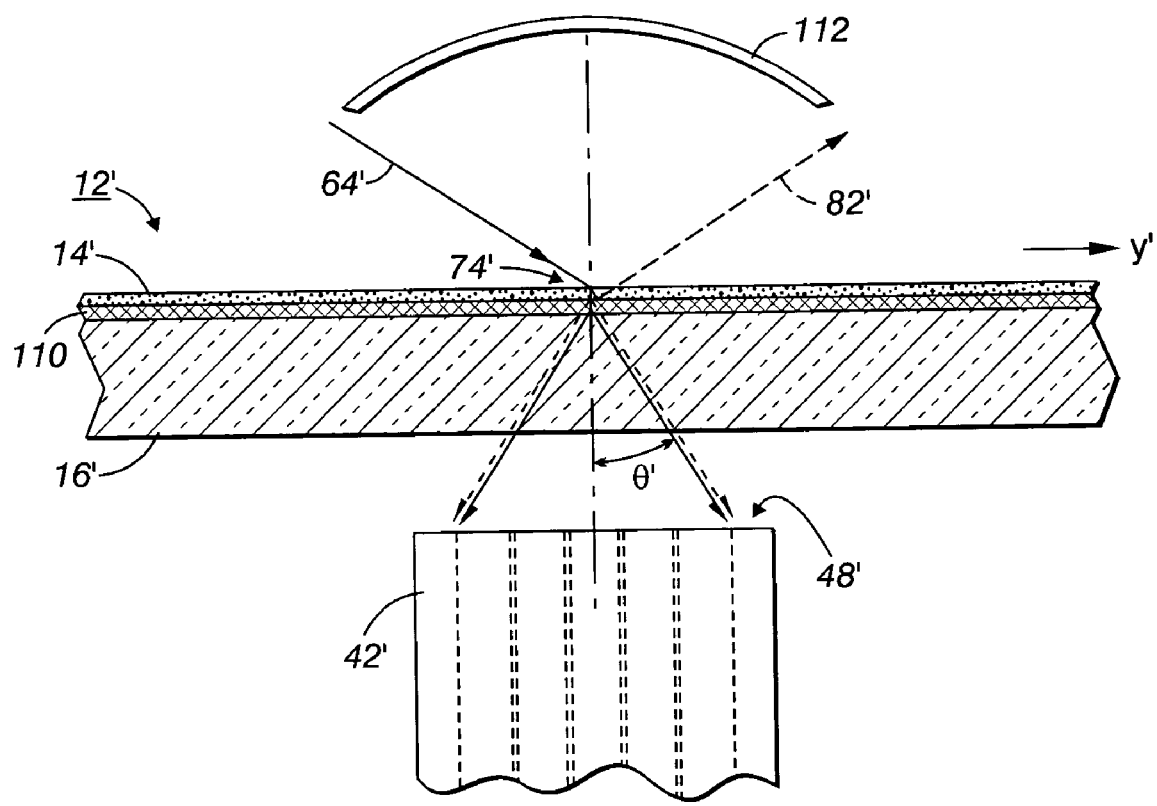
FIG. 5 shows a side view of another preferred embodiment of the invention, the view centered on the first end of the morphed fiber optic bundle.

With reference to FIG. 5, an alternative configuration of the scanning radiation source and the microscope aperture are described. In FIG. 5, elements which correspond to similar elements of the embodiment of FIGS. 1-4 are indicated by primed reference numbers, while new elements are indicated with unprimed reference numbers. In the embodiment of FIG. 5, a sample 12' includes a biological smear 14' coating an imager slide 16' similarly to the sample 12. A radiation beam 64' impinges upon the sample 12' along a trajectory 74' perpendicular to a y'-direction in an orientation substantially similar to that shown in FIG. 4. An input aperture 48' is substantially similar to the input aperture 48 of FIGS. 1-4, and is defined by a first fiber bundle end 42'.

However, in the embodiment of FIG. 5 the input aperture 48' is arranged to view the sample 12' from below, i.e. from a side of the slide 16' that is opposite the biological smear 14'. That is, the input aperture 48' views the biological smear 14' through the slide 16', which is light-transmissive for the characteristic luminescence of the cells. The input aperture 48' has a short dimension along the y'-direction and a long dimension perpendicular to the y'-direction, and has a light collection angle θ'.

Because the slide 16' is substantially light-transmissive for the characteristic luminescence, characteristic luminescence directed toward the input aperture 48' and lying within the light collection window defined by the collection angle θ' passes through the slide 16' and is collected by the input aperture 48' and transmitted to an output aperture (not shown in FIG. 5) similarly to the embodiment of FIG. 1.

The slide 16' includes an optional laser blocking filter 110, such as an absorption band pass filter, coating the surface below the biological smear 14'. The laser blocking filter 110 reflects substantially all the radiation beam 64' to form a reflected beam 82'. Because the laser blocking filter 110 substantially prevents scattered components of the radiation beam from reaching the input aperture 48', an element corresponding to the laser-blocking filter 94 of the embodiment of FIG. 1 is optionally omitted in the embodiment of FIG. 5, i.e. is functionally replaced by the laser blocking filter 110. It will be appreciated that the laser blocking filter 110 can alternatively be disposed on an opposite side of the slide 16, i.e. on the side facing the input aperture 48'. In yet another contemplated variation, the slide 16' is light transmissive for the characteristic luminescence, but is substantially absorbing for the excitation radiation of the radiation beam 64', so that the slide 16' itself serves as the laser-blocking filter.

The embodiment of FIG. 5 also includes an optional cylindrical reflector 112 having a linear focal line generally coinciding with the radiation beam trajectory 74' on the biological smear 14'. The cylindrical reflector 112 reflects characteristic luminescence directed away from the input aperture 48' back through its generation point on the beam trajectory 74' and into the input aperture 48'. The cylindrical reflector 112 can improve the signal-to-noise ratio for certain imaging applications by increasing the amount of characteristic luminescence that is collected. It will be recognized that the cylindrical reflector 112 can also be used in conjunction with the configuration of FIGS. 1-4.

As discussed above, the imager of the present discussion may be implemented both in luminous and non-luminous applications. When designed for use in a non-luminous implementation, the blocking filter is not required. When used in luminous applications, the blocking filter is required, and that filter may be an absorptive filter located at the slide or substrate, may be the fiber bundle itself, or may be a filter located in the output optics section. Another filter which is noted to be used in luminous applications is a reflective or interference type filter, which may be coated on the slide or substrate, or located in the output optics.

Figure 6:
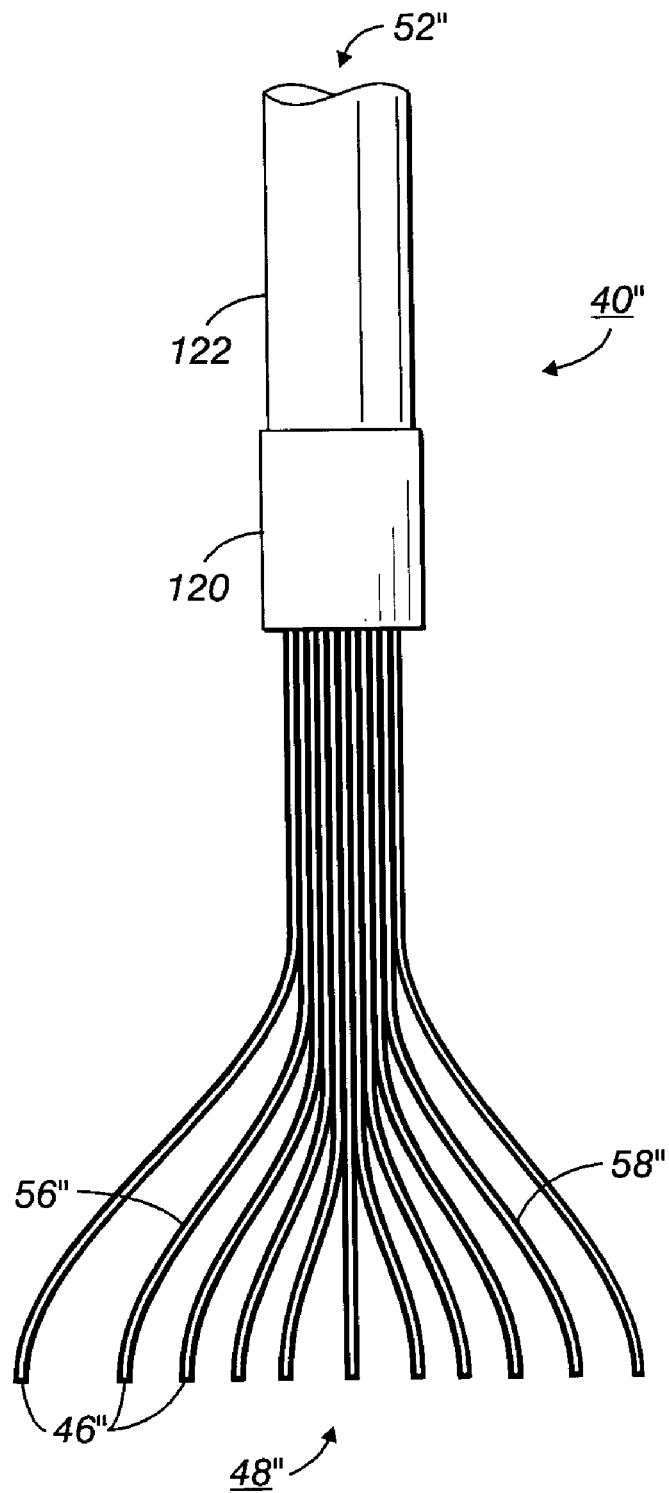
FIG. 6 diagrammatically shows another fiber optic bundle embodiment that is suitable for use in the apparatus of FIGS. 1-4 or the apparatus of FIG. 5.

With reference to FIG. 6, an alternative fiber optic bundle 40' is described, which is suitable for use in the apparatus embodiments of FIGS. 1-4 and FIG. 5. In FIG. 6, elements which correspond to similar elements of the optical fiber bundle 40 are indicated by double-primed reference numbers, i.e. a fiber optic bundle 40", while new elements are indicated with unprimed reference numbers. The optical fiber bundle 40" includes a plurality of first fiber ends 46" that collectively define a linear or high aspect ratio rectangular input aperture 48" that is similar to the input aperture 48. In FIG. 6, only a few fiber ends 46" are shown in schematic fashion. Preferably, the number of first fiber ends is in a range of thousands to tens of thousands or more. Each first fiber end 46" is a termination of a fiber, such as exemplary fibers 56", 58".

However, unlike the fiber optic bundle 40, the optical fibers 56", 58" of the fiber optic bundle 40" do not extend completely through to an output aperture 52". Instead, the optical fibers 56", 58" terminate at an optical coupler 120 which operates in known ways to combine light channeled by the plurality of fibers including the fibers 56", 58" into a single optical fiber or light pipe 122 which has a large diameter compared with the first fiber ends 46". The light pipe 122 has an end distal from the optical coupler 120 which defines the output aperture 52". Optionally, the distal end is narrowed, shaped to define a lensing surface, or otherwise modified (not shown in FIG. 6) to improve optical coupling with the output aperture 52". Although light pipe 122 is shown as straight in FIG. 6, it is to be appreciated that the light pipe 122 can be a rigid bent light pipe or a flexible light pipe. The optical fiber bundle 40" suitably substitutes for the optical fiber bundle 40 in FIGS. 1-4, or for the optical fiber bundle of the embodiment of FIG. 5.

Although the embodiments have been described with particular reference to cell identification, the invention is not limited in application thereto. The imager apparatus 10 of FIG. 1 is suitable for many imaging applications in which features are to be identified or located. In one such application lying in the biomedical arts, an array of typically ten to ten thousand DNA elements are arranged in an array known in the art as a DNA chip. The DNA elements are processed so that selected elements include a fluorescent tag. The apparatus of FIG. 1 is suitable for identifying the tagged DNA elements in a DNA chip that includes a large number of DNA elements. Implementing the concepts described in the foregoing permits for an imaging apparatus that can access the sample several times faster than existing technology.

Although the illustrated embodiments have been described with reference to detecting luminescence generated by tagged or treated cells, the imaging apparatus 10 is readily modified to detect other types of light signals. For example, the radiation beam 64 produced by the laser 62 typically produces scattered light as well as reflected light 82. The scattered light can be used for imaging by omitting the laser blocking filter 94 (or the laser blocking coating 110 in the embodiment of FIG. 5) so that the photodetector 98 is coupled to the output aperture to receive and detect the scattered laser light. The imaging apparatus 10 with laser blocking omitted is suitable for use in the electronics arts to identify non-specular defects on a polished semiconductor wafer. For epitaxial wafers with high quality epitaxial semiconductor films deposited thereon, or for wafers processed in a high-quality cleanroom environment, defects typically occur at low areal densities, and so are particularly suitable for characterization by the apparatus 10. Measured defect counts can be used for quality control screening in a wafer fabrication process.

Similarly, the imaging apparatus 10 is readily modified to image using the reflected beam 82. In addition to omitting the filter 94 (or film 110) as discussed in the previous paragraph, for this imaging mode the geometry shown in FIG. 4 is preferably adjusted so that the reflected beam 82 falls within the collection angle θ of the input aperture 48. To avoid having the input aperture 48 block the incident beam 64, the adjustment preferably includes tilting the input aperture 48 toward the reflected beam 82. That is, the input aperture 48 is positioned at a tilt relative to a surface normal of the imaged surface. The reflected beam imaging mode is suitable for counting or imaging low-density non-specular defects on polished surfaces of various types. The non-specular defects are imaged as decreases in the intensity of the reflected beam 82.

In yet another operating mode, the transmitted beam can be used for imaging. For example, the configuration of the embodiment of FIG. 5 can be modified by removing the laser blocking filter 110 and the cylindrical reflector 112 and tilting or translating the input aperture 48' to admit the transmitted portion of the radiation beam 64'. The radiation beam 64' is angularly adjusted to enter the input aperture 48'. For this imaging mode, a normal incidence of the radiation beam on the imaged surface can be suitable. An application of the transmission imaging mode is detection and counting of pinholes in opaque coatings, or recording light transmission differences in biological, organic, artificial or natural samples.

Figure 7A:
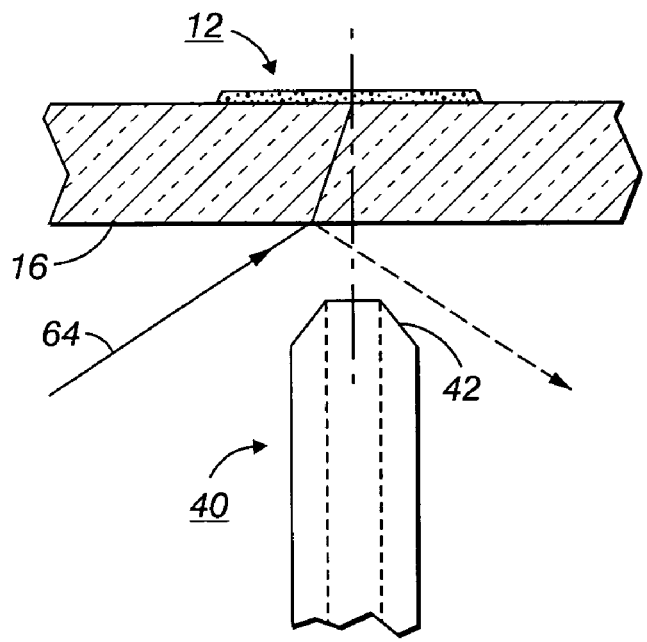

Turning to FIGS. 7A-7D, provided is a simplified illustration summarizing possible permutations for the relationship between the fiber optic bundle 40, radiation beam 64, slide 16 and sample 12. It is to be noted these permutations maybe employed for each of the embodiments, applications and uses described in the foregoing discussion. With specific attention to FIG. 7A, the simplified fiber optic bundle 40, or other described fiber optic acquisition design, is shown positioned below slide 16 which is carrying on its front surface sample 12. First end 42 of bundle 40 is near slide 16. Further shown in FIG. 7A is radiation beam 64 projecting towards sample 12 from the underside of slide 16. In this embodiment the radiation beam is entering slide 16 at 60° to normal, although it is to be understood other angles are possible. Beam 64 is shown bending toward the normal inside slide 16 to reach sample 12. Such bending of the light being in accordance with Snell's Law.

Figure 7B:
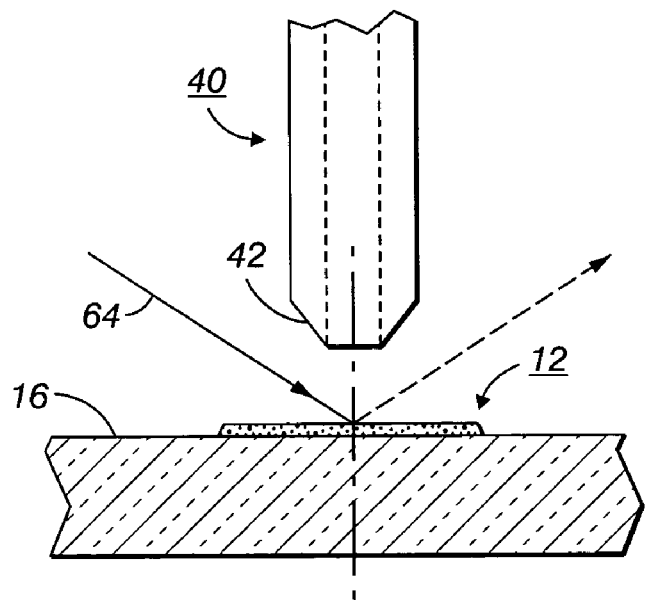

FIG. 7B represents an arrangement which has been described in reference to, for example, the previous figures such as FIG. 1. More specifically, the fiber optic bundle 40 having first end 42 closest to the sample 12 has radiation beam 64 interacting with sample 12 on the same side of slide 16. It is to be noted with regard to FIGS. 7A and 7B that the fiber optic bundle includes angled areas on the first end 42 such that the beam is not interfered with and the desired light collection is obtained. More specifically, as the excitation beam is projected to the slide and reflected off of the slide, interference is avoided via the angling of the first end 42.

Turning to FIG. 7C, set forth is a permutation wherein the fiber optic bundle 40 is located beneath slide 16 and on the opposite side of sample 12. Radiation beam 64 is shown interacting with sample 12 on a front surface of slide 16, and has an angled side as in FIG. 7C. Further, fiber optic bundle 40 includes a single angled side to avoid undesirable reflectivity.

Lastly, FIG. 7D sets forth a permutation where the fiber optic bundle 40 is located on the same side as sample 12 carried on slide 16. The radiation beam 64 is shown interacting with sample 12 via a back side of the slide 16. By this design, the excitation beam 64 travels through slide 16, and therefore is again affected by Snell's Law.

Each of the permutations may be used dependant upon the application. These designs permit a varying of the amount of excitation beam which may be collected and/or how close the fiber optic bundle head may be located to the slide.

The apparatuses and methods disclosed in the various embodiments teach high-speed scanning and detection which scans a sample to locate fluorescent dye-marked rare cells. This system will also detect cells identified by other types of cell marking mechanisms, such as quantum dots and DNA nano-particle probes. The described embodiments provide a system that may scan approximately up to 100,000 cells per second or more, depending upon the arrangement of the input aperture, the size of the laser beam and the speed of the scan. The system can detect fluorescence to a resolution of a cell and accurately determines and records the position of the fluorescing cells.

The foregoing thus describes fiber array scanning technology (FAST) that increases the speed at which scanning of a sample and detection of rare cells may be accomplished, it therefore lends itself to the investigation of large samples. A particular benefit of scanning large samples is particularly relevant to the investigation of rare cells, where the potential of false negative results are of specific concern. A false negative result indicates a particular type of cell was not found, when in fact the cell does exist. This result may lead to potential misdiagnosing of a patient as healthy when, in fact, a medical problem exists.

Cell detection systems presently in use commonly place the samples on a slide having a dimension of 2.5 by 7.5 centimeters (or about 1 inch by 3 inches). Using the scan techniques of the present application, large sample areas may be scanned efficiently, and samples of 7.5 centimeters by 12.5 centimeters (or about 3 by 5 inches), 15 by 15 centimeters (or about 6 by 6 inches) or larger may be used. Again, one of the reasons for the speed of the described scanning process is use of the wide input aperture that nevertheless permits sufficiently high resolution to detect the rare cells.

Figure 8A:
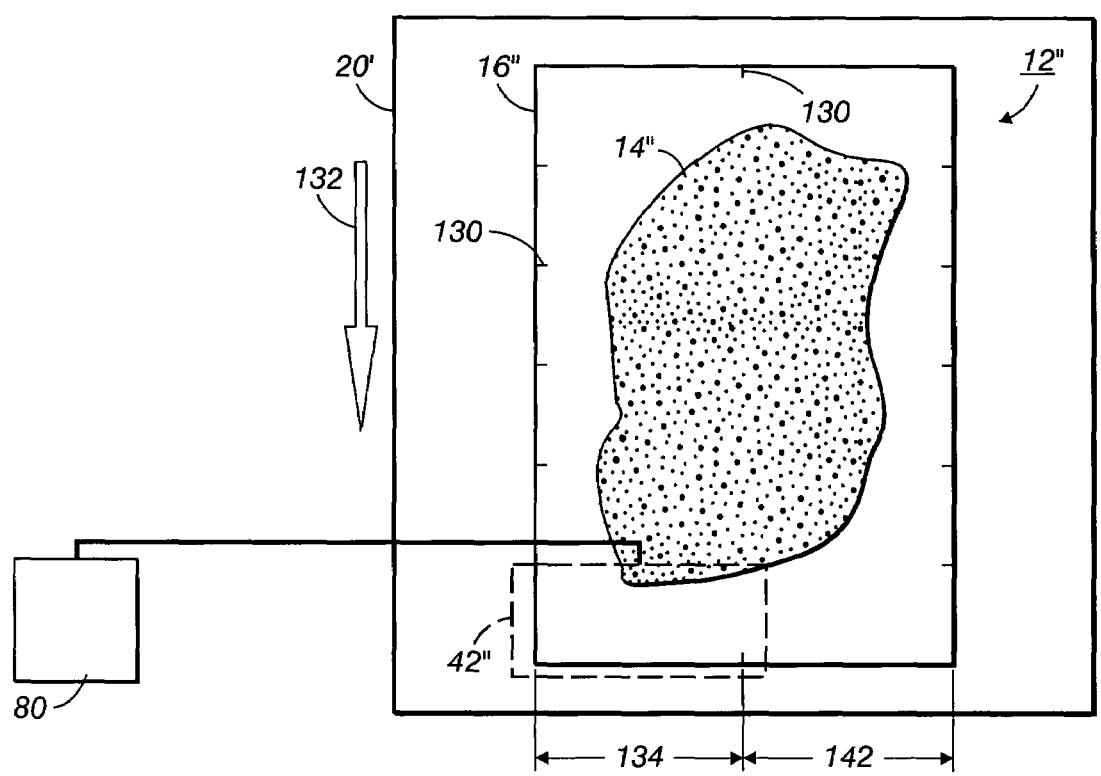
FIGS. 8A-8C illustrate an enlarged sample area and an embodiment for a higher resolution investigation.
Figure 8B:
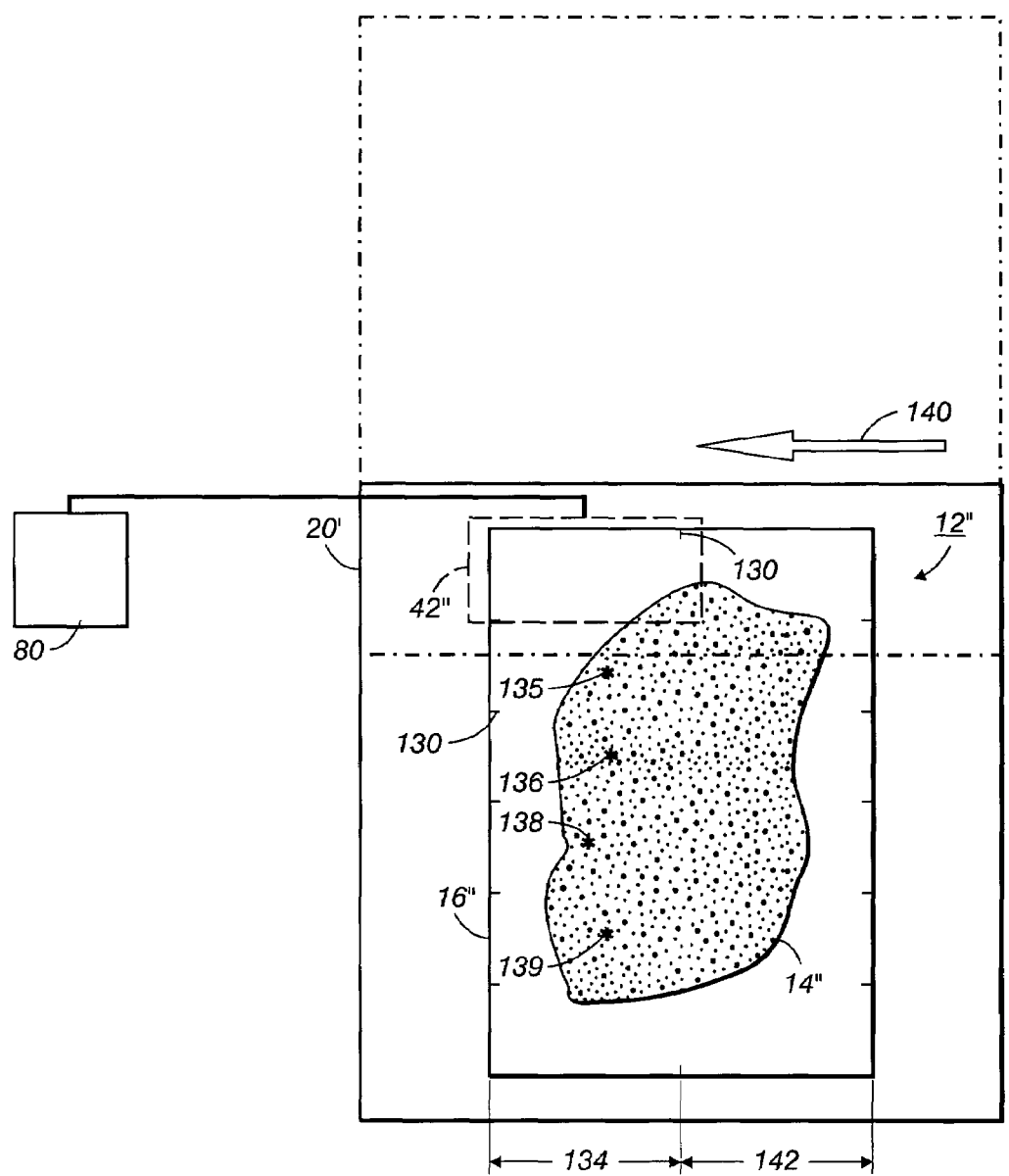
Figure 8C:
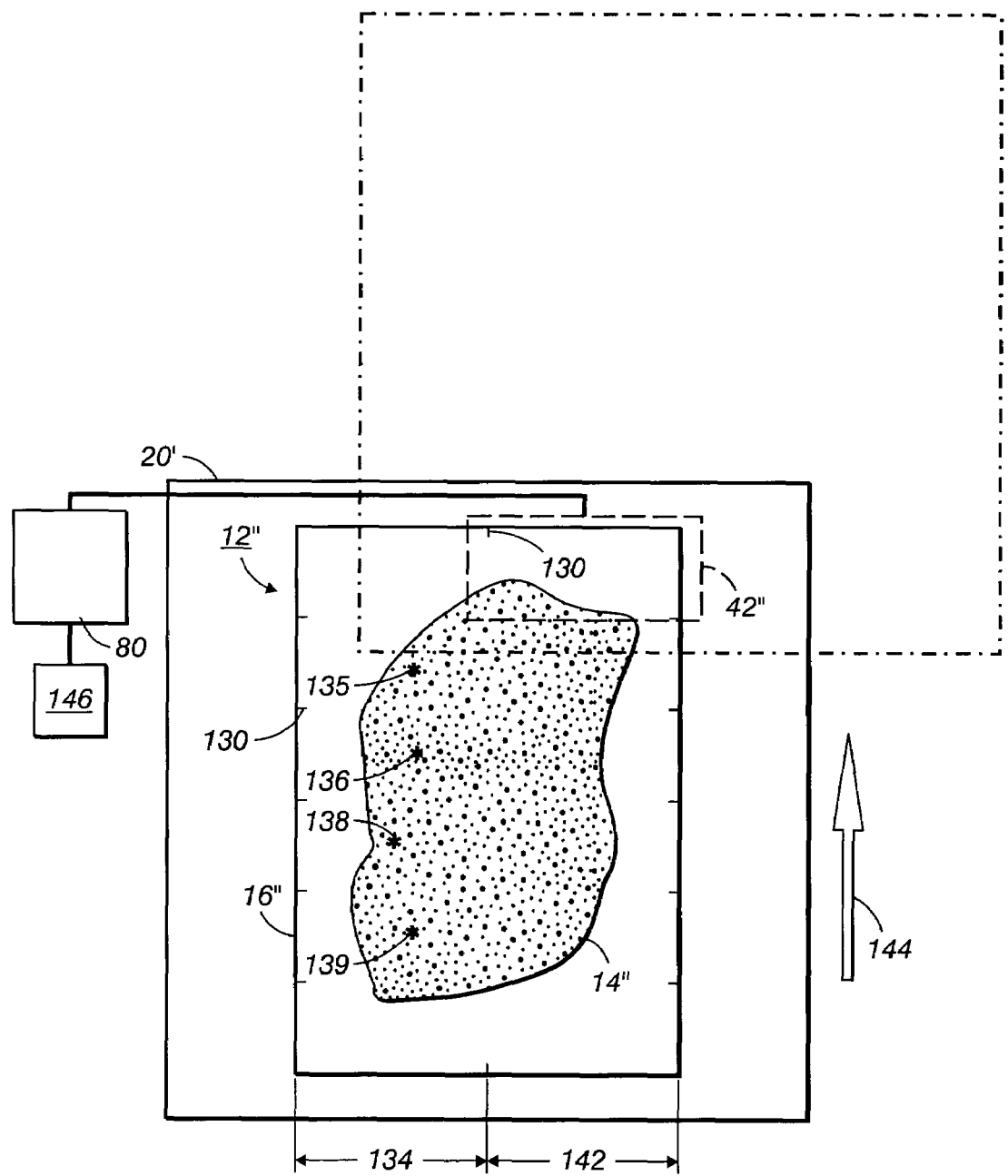

An implementation of scanning large samples is now described with attention to FIGS. 8A-8C. The top view of FIG. 8A illustrates that a sample 12", such as a biological smear 14" disposed on at least a portion of a surface of a slide 16", is wider than first end 42" which forms an input aperture such as input aperture 48 of FIG. 1. The sample 12" is on translation stage 20' in a manner illustrated, for example, with the gearing and structural arrangement shown in FIG. 1.

Slide 16" incorporates registration marks 130 to assist in obtaining positional information of detected rare cells to be identified and saved. As noted in previous sections of this application, the position identification information may be obtained through use of registration marks or through other position detection techniques.

In either case, the translation stage 20' is operated in accordance with the gearing shown in FIG. 1. As the translation stage is moved in the direction of arrow 132(i.e., arrows 28 of FIG. 1), the input aperture of first end 42", in conjunction with the laser scanning operations previously described, acts to detect and identify fluorescing cells within a first portion 134 of sample 12". The translation stage continues until the total area of first portion 134 has been scanned as depicted in FIG. 8B.

Based on this operation, cells 135, 136, 138, 139 are detected. These cells, again, may be cancer cells, fetal cells, bacteria or other cells for which fluorescence markers, quantum dots, DNA nano-particle probes or other marking processes have caused the cells to be identified. The cells, for example, may also be those of other organs of a body, such as liver cells, brain cells, for which markers are developed. Once the translation stage has moved sample 12" to the position noted in FIG. 8B, translation stage 20' is moved in the x direction (arrow 140) indexing the sample such that a second portion 142 of the sample is under the input aperture of first end 42, as shown in FIG. 8C. Thereafter, translation stage 20' is moved in the direction shown by arrow 144 to scan the second portion 142. It is to be appreciated that while one particular scanning sequence is shown, other sequences may be used. A slight overlap may exist between the first portion 134 and second portion 142 to ensure scanning of the entire sample. Position data is maintained by known indexing or registration processes as previously discussed. Also, while FIGS. 8A-8C show only a first portion 134 and a second portion 142, sample 12" maybe larger, resulting in additional portions which will be scanned in a similar process.

In some instances the scanned sample will require processing following the identifying and localization of the cells of interest. At this point, the sample maybe removed for these additional actions. For example, once the cells are localized, they can be analyzed for genetic defects using conventional analysis tools like fluorescence in situ hybridization (FISH), or by use of an automated fluorescent microscope, as well as by other investigative systems.

Alternatively, in other situations, a benefit will exist to undertake further investigation as part of the imaging system itself. One of these instances is when the sample being investigated requires a higher resolution than may be obtained by the described system. Therefore, the system of the present application includes a further embodiment, wherein, as shown in FIG. 8C, controller 80 provides the location or positional information of the sample cells 135-139 to an automated high-resolution device 146, such as an automated fluorescent microscope. Once the scanning process has been completed (or during the process), the automated high-resolution device 146 is provided with the cell position information and it is activated to move and investigate the cells in greater detail. Movement of automated high-resolution device 146 may be obtained by translation/gearing arrangements that are well known in the art and similar as those previously described herein. This embodiment finds particular application when it is known or highly suspected a certain cell will be found, for example, when a patient is undergoing treatment for cancer. In this scenario, the integration of the high-resolution device 146 will increase the speed of review.

In the preceding discussion it may be considered that a single type of marker was provided on sample 12", such as one that will attach to one particular type of cancer cell. However, alternative embodiments of the present system include providing the biological smear 14" of sample 12" with a plurality of markers which will attach to different cells of characteristics of a cell type, and which react at distinctly different frequencies of light. Therefore, in one embodiment, sample 12" may include markers which are intended to identify different types of cancer cells (e.g., brain cancer, colon cancer, lung cancer, etc.).

When multiple distinct markers are incorporated into a single sample 12", the scanning radiation source 60, which includes a laser 62 or other light source, may be configured, in one embodiment, to emit radiation beam 64 at multiple distinct frequencies that correspond to the frequencies at which the individual distinct markers are designed to react. In other embodiments, such as when using quantum dots for markers where excitation frequencies are best left to a single frequency, the illumination frequency might not be varied. Thus, during a first pass the scanning radiation source 60 can operate to scan the sample 12" at a first frequency designed to obtain data corresponding to first markers. In this example, the first markers equate to cells 135 and 138.

Following this first pass, the sample is rescanned, and the scanning radiation or light source 60 is operated at a second frequency, which causes second markers to become fluorescent. In this example, the second markers are attached to cells 136, 139. Additional scanning at further frequencies may take place when sample 12" includes further unique markers.

In this embodiment, blocking filter 94, may be considered a filter arrangement that includes the blocking characteristics previously described, and in addition is tunable and/or variable such that there is a correspondence between the frequency of operation of the scanning radiation or light source 60, the marker being sought, and the light being filtered. In one implementation, an appropriate filter is to be manually moved into position, dependent on the frequency of the light source and/or the marker being sought. For example, in a first instance at a first frequency, filter arrangement 94 permits the first frequency to pass, while blocking other operational frequencies (i.e., second frequency and third frequency, etc.). By this configuration, the system is capable of identifying and locating multiple cell types in a single sample. In this embodiment, imager 10 undertakes multiple scans.

In an alternative embodiment, the scanning radiation or light source 60 is configured to substantially simultaneously emit a plurality of distinct beams to sample 12". To obtain the plurality of distinct beams, laser 62 may be a plurality of lasers positioned to emit their beams to the input aperture 42. In such an embodiment, the input aperture 42 of FIG. 1 collects the multiple sources of light during a single scan, and this light is transmitted to second end 44.

Blocking filter arrangement 94 is to be constructed to permit each of the appropriate frequencies (i.e., first frequency, second frequency, etc.) to pass to photodetector arrangement 98. In this instance, photodetector arrangement 98 is designed to differentiate between the frequencies of the light generated at the various frequencies. In one embodiment, the ability to differentiate between the different light frequencies, may be accomplished by measuring the amount of energy detected by a photodetector and calibrating that value to one of the multiple emitted beam frequencies. This design permits a differentiation between the cell types being detected. Thus, multi-beam scanning during a single pass may be obtained.

In an alternative arrangement for this multi-beam, single-pass embodiment, differentiation may be accomplished by an arrangement of beam splitters and mirrors that direct individual beams of a particular frequency to specific distinct photodetector configurations.

Figure 8D:
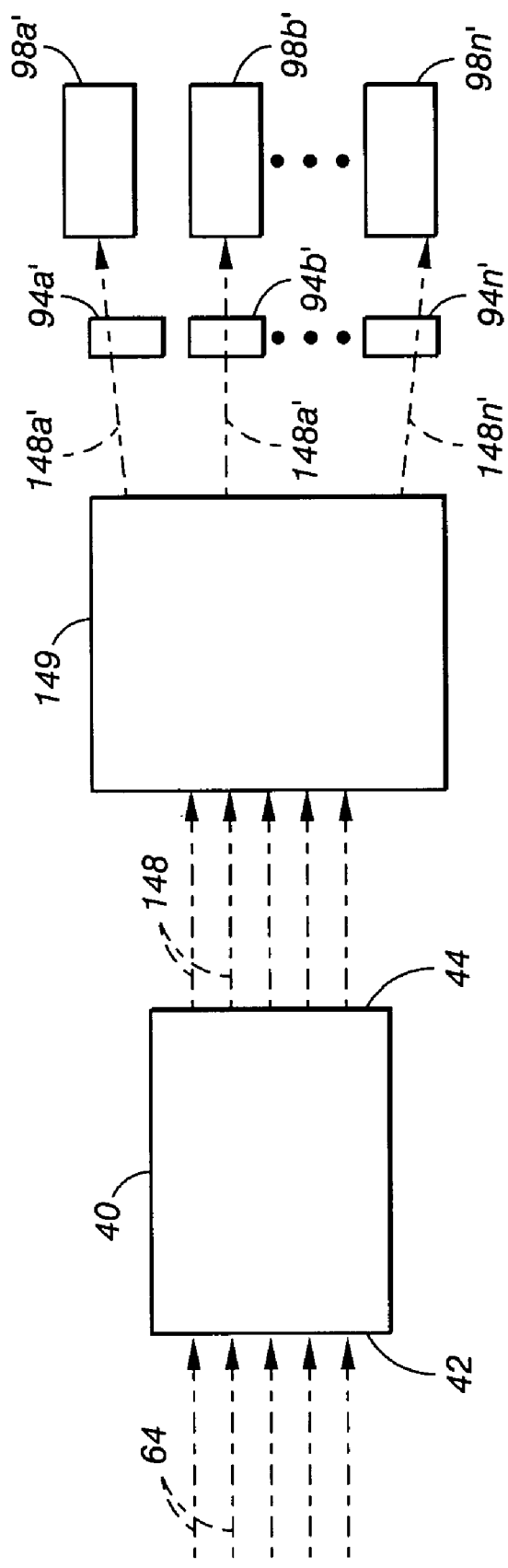
FIG. 8D illustrates a design for a multi-beam single pass embodiment.
Figure 9:
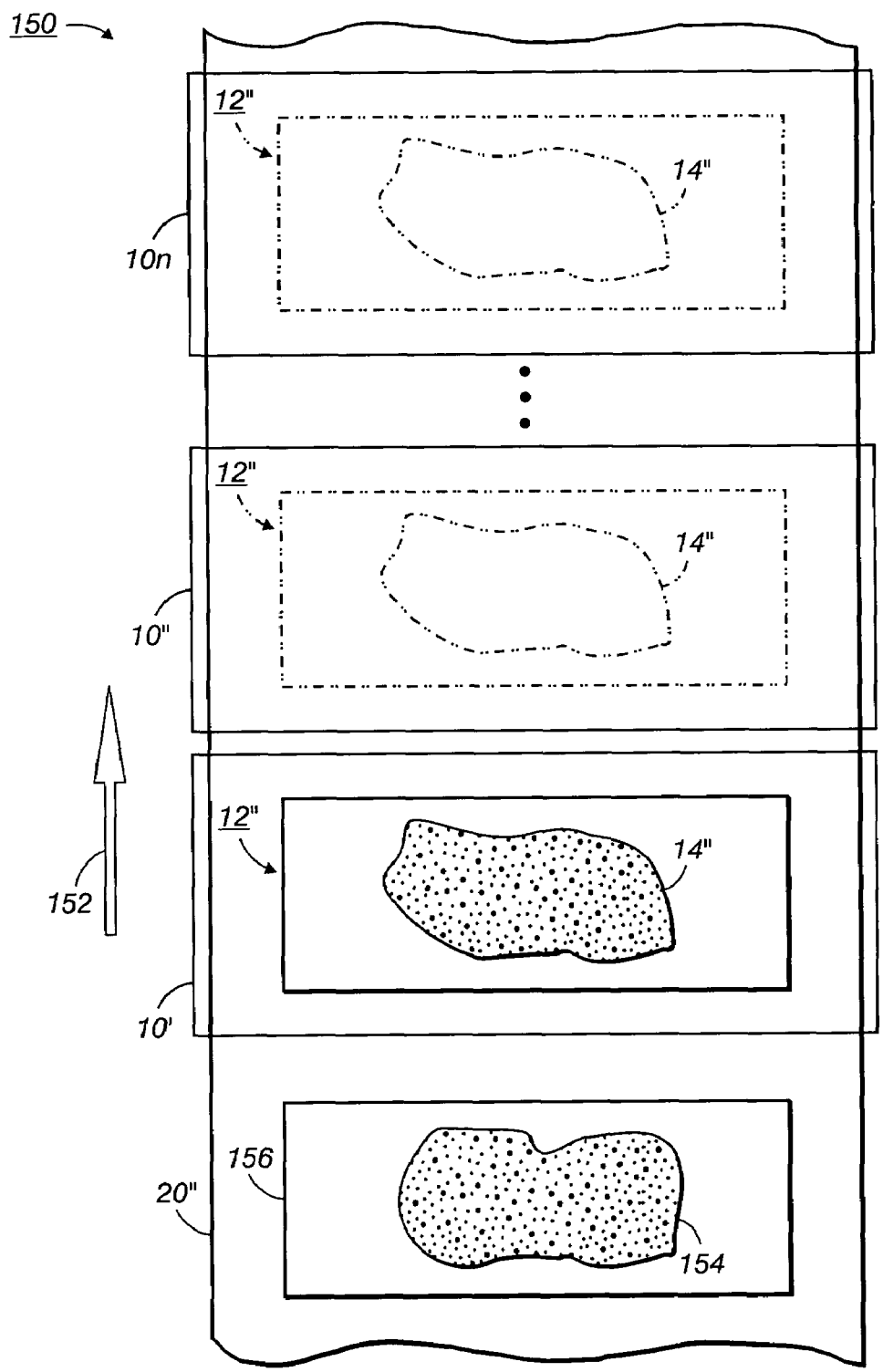
FIG. 9 illustrates a conveyor-type process for scanning in accordance with the present application.

One example of such an embodiment is shown in FIG. 8D. Beam 64' represents a first frequency of light, which causes light to be collected at the first end 42 of fiber optic bundle 40 and emitted from second end 44. The emitted light 148 is directed to a beam-splitting arrangement 149. The beam-splitting arrangement may be a known beam splitter such as an acousto-optic cell (AO), a multi-faceted mirror, or other deflecting arrangement. Beam 148 is then split into sub-beams 148a', 148b', 148n' directed to filter arrangements 94a', 94b', and 94n', respectively. The filter arrangement 94a'-94n' are designed or tuned to permit passage of a selected frequency. For example, in this instance filter arrangement 94a' is designed to pass the first frequency and to block other frequencies. Similarly, filter arrangements 94b' and 94n' will pass a second frequency and third frequency, respectively, while blocking others. Thus, in this instance, the first frequency part of beam portion 148a' impinges on photodiode arrangement 98a', whereas the first frequency part of beams 148b' and 148n' is blocked by filter arrangements 94b' and 94n', whereby the light having the first frequency does not fall on photodiode detectors 98b' and 98c'. Though not shown in this design, clearly the individual optic couplers will be connected in a manner similar to FIG. 1 and to the control electronics necessary for operating the device. Also, the additional filtering and connection elements of FIG. 1 may easily be incorporated into this design.

In still a further embodiment, as shown in connection with FIGS. 8A-8D, FIG. 1 and FIG. 9, a sample 12" having a plurality of marker types, may be scanned in a conveyor-type system 150, where each scan is directed to a single marker type. Particularly, sample 12" holding smear 14" is scanned in a first instance by an imaging apparatus or imager 10' configured and designed such as shown in FIG. 1. While sample 12" is being imaged by imager 10', the sample is being moved in direction 152. Following a complete scan as previously described, the sample 12" is then moved to a next imager 10", which again is the same as that described in connection with FIG. 1. At this point, sample 12" will be scanned at a second frequency different from the first frequency. By this arrangement, cells which have markers attached that function at a second frequency, will be detected. Following this operation, the process continues to move on through successive stages of imagers to 10$_n$ until a scan for all markers of the sample has been accomplished. While there is a certain latency delay at the beginning of an operation, using this conveyor type system permits multiple samples to be efficiently scanned once the latency is addressed. Specifically, following the scanning of sample 12", a next sample 154 immediately follows sample 12", thus filling up the queue of movement. Samples 12" and 154 are carried on translation table 20' (or 20 of FIG. 1). Therefore, in this design each of the imagers 10', 10" and 10$_n$ are positioned such that scanning of samples occurs at the same time and/or position in order to maintain proper synchronization of the transport system. Alternatively, this design may be implemented with a number of individual translation tables 20' (20), which are close enough together to pass a sample from one to the other, but once received will individually control movement of the received sample. Still further, an intermediate translation table may be located between two scanning translation tables. The intermediate translation table being used to simply pass the sample from a first scanning translation table to a second translation table. The scanning translation tables being the tables where the actual scanning operations occur. Both the intermediate and scanning translation tables may be constructed in accordance with the teachings of FIG. 1.

In still a further alternative embodiment, the high-resolution device 146 is positioned in a fixed relationship to the input end 42" such that it is located substantially immediately over a rare cell after detection by input end 42". In this embodiment, the imaging system, including the movement of translation table 20' and the laser scanning arrangement (not shown) is mechanized to permit the investigation if required.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An imaging method for detecting rare cells comprising:
sweeping a radiation beam along a scan path on a sample;
moving the sample generally perpendicularly to the scan path of the radiation beam sweeping, the moving cooperating with the sweeping so that the beam illuminates the entirety of the sample;
collecting light produced by beam interaction with the sample using at least one proximate element of an array of fiber optic first ends;
transmitting the collected light along a fiber associated with the at least one proximate element, the fiber channeling the collected light to a selected output region including an array of fiber optic second ends, wherein an arrangement of the array of fiber optic first ends is distinct from an arrangement of the array of fiber optic second ends;
detecting the collected light at the selected output region; and
coordinating the sweeping, moving, and detecting to generate an array of picture elements representative of at least a portion of the sample.

2. The method according to claim 1, wherein the sample includes a biological smear designed to identify rare cells from at least one of an organ or tissue of a body.

3. The apparatus according to claim 2, wherein the biological smear is designed to identify at least one of cancer cells, fetal cells, bacteria cells, kidney cells, liver cells, brain cells, cells expressing certain antibodies, or cells expressing with certain proteins.

4. The imaging method as set forth in claim 1, wherein the sample includes a biological smear, the imaging method further including:
marking the biological smear using a fluorescent material that selectively attaches to a selected type of cell, wherein the light produced by beam interaction includes fluorescence produced by the fluorescent material due to interaction with the radiation beam.

5. The method according to claim 4, wherein the step of marking the biological smear using a fluorescent material further includes using a plurality of fluorescent materials, at least some becoming fluorescent at lightwave frequencies different from each other.

6. The method according to claim 5, wherein the step of sweeping a radiation beam further includes sweeping a plurality of radiation beams at different wavelengths, the different wavelengths corresponding to the wavelengths at which the different fluorescent materials become fluorescent.

7. The method according to claim 6, wherein the step of sweeping the plurality of radiation beams at different frequencies occurs non-concurrently with each other.

8. The method according to claim 6, wherein the steps of sweeping the plurality of radiation beams at different frequencies occurs substantially simultaneously with each other.

9. The method according to claim 1, further including a step of filtering the array of generated picture elements to differentiate between those picture elements representing rare cells and those picture elements representing structures other than rare cells.

10. The method according to claim 9, wherein the filtering step investigates characteristics of the differentiated picture elements, the characteristics including at least one of an amount of differentiated picture elements, an intensity of the differentiated picture elements, the phase of the differentiated picture elements, or a shape of the differentiated picture elements.

11. An apparatus for identifying rare cells in a biological smear, the rare cells emitting a characteristic luminescence responsive to exposure to an excitation radiation, the apparatus including:
a translation stage that supports the biological smear;
a fiber optic bundle having a proximate bundle end of first fiber ends arranged to define an input aperture viewing the biological smear on the translation stage, and a distal bundle end of second fiber ends arranged to define an output aperture shaped differently from the input aperture and disposed away from the translation stage;
a scanning radiation source arranged in fixed relative position to the input aperture, the scanning radiation source scanning a radiation beam on the biological smear within a viewing area of the input aperture, the radiation beam interacting with the biological smear to produce a light signal that is received by the input aperture and transmitted via the fiber optic bundle to the output aperture;
a photodetector arranged to detect the light signal at the distal bundle end; and
a processor that processes the light signal detected by the photodetector to identify existence of rare cells in the biological smear.

12. The apparatus according to claim 11, wherein the biological smear is designed to identify at least one of cancer cells, fetal cells, bacteria cells, liver cells, cells expressing certain antibodies, or cells expressing certain proteins or brain cells.

13. The apparatus according to claim 11, further including a controller which generates position information of at least one identified rare cell in the biological smear.

14. The apparatus according to claim 13, further including an automated high-resolution device, arranged to receive the position information of the at least one rare cell, and to automatically move to the location of the at least one biological smear.

15. The apparatus according to claim 11 where the biological smear contains at least 20 million cells.

16. The apparatus according to claim 11, wherein the biological smear contains at least 50 million cells.

17. The apparatus according to claim 11, further including:
a motor arranged to move the sample in one of a translational and a rotational motion, the motor cooperating with the scanning radiation source to effectuate a rastering of the radiation beam over a selected area of the biological smear.

18. The apparatus according to claim 17, wherein the input aperture has a generally linear shape, the scanning radiation source scans the radiation beam along a beam trajectory parallel to the generally linear aperture, and the motor linearly translates the sample along a trajectory that is perpendicular to the beam trajectory.

19. The apparatus according to claim 18, wherein the motor rotates the sample about an axis that is normal to a surface of the sample, the input aperture has a generally linear shape extending radially away from the rotational axis, and the scanning radiation source scans the radiation beam along a beam trajectory parallel to the generally linear aperture.

20. The apparatus according to claim 11, wherein the light signal is a fluorescence generated by interaction of the radiation beam with a rare cell in the biological smear.

21. The apparatus according to claim 20, wherein the fluorescence generated by interaction of the radiation beam with the biological smear includes the biological smear being formed with at least one of fluorescent dye, quantum dots or DNA nano-particle probes.

22. The apparatus according to claim 11, wherein the biological smear includes a plurality of distinct markers, used to identify distinct cells or portions of cells.

23. The apparatus according to claim 11, wherein the scanning radiation source generates a plurality of radiation beams at a plurality of distinct wavelengths, wherein the distinct wavelengths correspond to the distinct markers.

24. The apparatus according to claim 11, wherein the fiber optic bundle is a first fiber optic bundle and the scanning radiation source is a first scanning radiation source, and the apparatus further includes,
a second fiber optic bundle,
a second scanning radiation source, and
the second fiber optic bundle and the second scanning radiation source are a distance from the first fiber optic bundle and the first scanning radiation source, wherein the translation stage is configured to move the sample from the first fiber optic bundle and the first scanning radiation source to the second fiber optic bundle and the second scanning radiation source.

25. An imaging method comprising:
sweeping a radiation beam along a linear path on a first portion of a sample;
moving the sample in a first direction generally perpendicularly to the linear path of the radiation beam sweeping, the moving in the first direction cooperating with the sweeping to raster the radiation beam on the sample;
collecting light produced by beam interaction with the first portion of the sample using at least one proximate element of an array of fiber optic ends;
transmitting the collected light along a fiber associated with the at least one proximate element, the fiber channeling the collected light to a selected output region, wherein a largest spatial dimension of the output region is substantially smaller than a largest spatial dimension of the array of fiber optic proximate ends;
detecting the collected light from the first portion of the sample at the selected output region;
moving the sample in a second direction, generally perpendicular to the first direction, a distance to a second portion of the sample;
sweeping the radiation beam along a linear path on a second portion of the sample;
moving the sample in a first direction generally perpendicularly to the linear path of the radiation beam sweeping, the moving in the first direction cooperating with the sweeping to raster the radiation beam on the sample;
collecting light produced by a beam interaction with the second portion of the sample using at least one proximate element of an array of fiber optic ends;
transmitting the collected light along a fiber associated with the at least one proximate element, the fiber channeling the collected light to the selected output region wherein the largest spatial dimension of the output region is substantially smaller than the largest spatial dimension of the array of fiber optic proximate ends;
detecting the collected light from the second portion of the sample at the selected output region; and
coordinating the sweeping, moving, and detecting to generate an array of picture elements representative of at least a portion of the first and second portions of the sample.

26. The method according to claim 25, wherein the sample is a biological smear designed to identify at least one of cancer cells, fetal cells, bacteria cells, liver cells or brain cells.

27. The method according to claim 26, wherein the light signal is a fluorescence generated by interaction of the radiation beam with a rare cell in the biological smear.

28. The method according to claim 27, wherein the fluorescence generated by interaction of the radiation beam with the biological smear, includes the biological smear being formed with at least one of fluorescent dye, quantum dots or DNA nano-particle probes.

29. An apparatus for identifying cells in a biological smear, the cells emitting a characteristic luminescence responsive to exposure to an excitation radiation, the apparatus including:
a translating stage that laterally translates the biological smear in a first direction and a second direction;
a fiber optic bundle including a plurality of fibers each having a first end and a second end, the first ends arranged to define a generally rectangular receiving aperture having a large aspect ratio, the second ends arranged to define an output aperture having a compact shape;
a radiation source that linearly sweeps an excitation radiation beam across the first portion of the biological smear with a sweep direction perpendicular to the first direction, an interaction region of the radiation source and a first portion of the biological smear being arranged relative to the receiving aperture such that characteristic luminescence produced in the interaction region is collected by the receiving aperture;
a controller that controls the translation of the translation stage in the first directions and the sweeping of the radiation source to raster the excitation radiation beam across the biological smear to identify rare cells in the first portion of the biological smear based upon the characteristic luminescence detected during the rastering, the controller further controls translation of the translation stage in a second direction to place a second portion of the biological smear in a position where the radiation source linearly sweeps the excitation radiation beam across the second portion of the biological smear with a sweep direction perpendicular to the first direction, an interaction region of the radiation source and the second portion of the biological smear being arranged relative to the receiving aperture such that characteristic luminescence produced in the interaction region is collected by the receiving aperture; and
a photodetector arranged to detect the collected characteristic luminescence of the first portion and the second portion of the biological smear at the output aperture.

30. The apparatus according to claim 29, wherein the biological smear is designed to identify at least one of cancer cells, fetal cells, bacteria cells, liver cells or brain cells.

31. The apparatus according to claim 29, further including a controller which generates a position information of at least one identified rare cell in the biological smear.

32. The apparatus according to claim 31, further including an automated high-resolution device, arranged to receive the position information of the at least one rare cell, and to automatically move to the location of the at least one biological smear.

33. The apparatus according to claim 32, wherein the high resolution device is an fluorescent microscope.

* * * * *